(12) United States Patent
Oetjen

(10) Patent No.: US 10,144,016 B2
(45) Date of Patent: Dec. 4, 2018

(54) APPARATUS FOR NON-CONTACT PRINTING OF ACTIVES ONTO WEB MATERIALS AND ARTICLES

(71) Applicant: The Procter & Gamble Company, Cincinnati, OH (US)

(72) Inventor: David Christopher Oetjen, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/335,913

(22) Filed: Oct. 27, 2016

(65) Prior Publication Data

US 2017/0120260 A1 May 4, 2017

Related U.S. Application Data

(60) Provisional application No. 62/248,546, filed on Oct. 30, 2015.

(51) Int. Cl.
*B05B 1/06* (2006.01)
*B05C 1/10* (2006.01)
(Continued)

(52) U.S. Cl.
CPC .......... *B05B 1/06* (2013.01); *A61F 13/15764* (2013.01); *B05C 1/10* (2013.01);
(Continued)

(58) Field of Classification Search
CPC ...................................................... B05B 1/06
(Continued)

(56) References Cited

U.S. PATENT DOCUMENTS 1,668,322 A * 5/1928 Kessler, Jr. ......... B41F 15/0836
101/116
1,867,314 A 7/1932 Gurwick
(Continued)

FOREIGN PATENT DOCUMENTS

DE 19854634 C1 2/2000
EP 1 075 948 B1 9/2005
(Continued)

OTHER PUBLICATIONS

All Office Actions and references listed in U.S. Appl. Nos. 14/291,588; 14/291,604; 14/291,631; 14/291,664; 14/291,691; 14/291,757; 14/291,823.
(Continued)

*Primary Examiner* — Leslie J Evanisko
(74) *Attorney, Agent, or Firm* — Sarah M. DeCristofar; Andrew J. Hagerty

(57) ABSTRACT

An apparatus for providing non-contact application of fluids onto web materials and articles is disclosed. The apparatus comprises a gravure roll having a hollow rotating shell having a plurality of cavities disposed within the outer surface thereof and a stationary cylindrical core having a central bore and a channel disposed therein. A fluid disposed within a respective cavity of the plurality of cavities disposed within the outer surface of the hollow rotating shell is removed from the respective cavity by the positive pressure when the positive pressure is fluidly communicated from the central bore through the channel and into the cavity from the surface of the stationary cylindrical core.

12 Claims, 15 Drawing Sheets

(51) Int. Cl.
*B05C 1/16* (2006.01)
*B05C 5/02* (2006.01)
*A61F 13/15* (2006.01)

(52) U.S. Cl.
CPC .............. *B05C 1/165* (2013.01); *B05C 5/025* (2013.01); *B05C 5/0233* (2013.01)

(58) Field of Classification Search
USPC .......................... 118/212, 213, 301; 101/114
See application file for complete search history.

(56) References Cited

U.S. PATENT DOCUMENTS

| | | | |
|---|---|---|---|
| 2,226,163 A | 12/1940 | DuFour | |
| 2,427,765 A | 9/1947 | Chollar | |
| 2,468,400 A | 4/1949 | Huebner | |
| 2,864,310 A | 12/1958 | Nelson | |
| 3,055,296 A | 9/1962 | Farrow | |
| 3,056,384 A | 10/1962 | Beale | |
| 3,294,016 A | 12/1966 | Heonis | |
| 3,301,746 A | 1/1967 | Sanford et al. | |
| 3,473,576 A | 10/1969 | Amneus | |
| 3,573,164 A | 3/1971 | Friedberg et al. | |
| 3,738,269 A | 6/1973 | Wagner | |
| 3,821,068 A | 6/1974 | Shaw | |
| 3,896,722 A | 7/1975 | Farrow | |
| 3,896,723 A | 7/1975 | Farrow et al. | |
| 3,974,025 A | 8/1976 | Ayers | |
| 3,994,771 A | 11/1976 | Morgan, Jr. et al. | |
| 4,033,258 A | 7/1977 | Farrow | |
| 4,191,609 A | 3/1980 | Trokhan | |
| 4,191,756 A | 3/1980 | Masi et al. | |
| 4,239,065 A | 12/1980 | Trokhan | |
| 4,300,981 A | 11/1981 | Carstens | |
| 4,361,089 A | 11/1982 | Wittkopf et al. | |
| 4,437,408 A | 3/1984 | Arkans | |
| 4,440,597 A | 4/1984 | Wells et al. | |
| 4,452,141 A | 6/1984 | Mistyurik | |
| 4,458,399 A | 7/1984 | Kessler | |
| 4,483,053 A | 11/1984 | Hamisch, Jr. | |
| 4,526,098 A | 7/1985 | Bachman | |
| 4,528,239 A | 7/1985 | Trokhan | |
| 4,529,480 A | 7/1985 | Trokhan | |
| 4,534,094 A | 8/1985 | Kessler | |
| 4,550,681 A | 12/1985 | Zimmer et al. | |
| 4,574,732 A | 3/1986 | Verwey et al. | |
| 4,599,627 A | 7/1986 | Vollert | |
| 4,637,859 A | 1/1987 | Trokhan | |
| 4,766,840 A | 8/1988 | Beckley et al. | |
| 4,812,899 A | 3/1989 | Kueppers | |
| 4,844,952 A | 7/1989 | Korenkiewicz et al. | |
| 4,878,977 A | 11/1989 | Kueppers | |
| 4,939,992 A | 7/1990 | Bird | |
| 5,082,703 A | 1/1992 | Longobardi | |
| 5,282,419 A | 2/1994 | Barrois | |
| 5,316,582 A * | 5/1994 | Dubel .................. B05B 7/2483 118/213 |
| 5,364,504 A | 11/1994 | Smurkoski et al. | |
| 5,429,686 A | 7/1995 | Chiu et al. | |
| 5,458,590 A | 10/1995 | Schleinz et al. | |
| 5,529,664 A | 6/1996 | Trokhan et al. | |
| 5,549,790 A | 8/1996 | Van Phan | |
| 5,556,509 A | 9/1996 | Trokhan et al. | |
| 5,580,423 A | 12/1996 | Ampulski et al. | |
| 5,609,725 A | 3/1997 | Van Phan | |
| 5,629,052 A | 5/1997 | Trokhan et al. | |
| 5,637,194 A | 6/1997 | Ampulski et al. | |
| 5,672,248 A | 9/1997 | Wendt et al. | |
| 5,674,663 A | 10/1997 | McFarland et al. | |
| 5,679,222 A | 10/1997 | Rasch et al. | |
| 5,693,187 A | 12/1997 | Ampulski et al. | |
| 5,695,855 A | 12/1997 | Yeo et al. | |
| 5,709,775 A | 1/1998 | Trokhan et al. | |
| 5,713,275 A * | 2/1998 | Imai ........................ B41L 13/18 101/119 |
| 5,714,041 A | 2/1998 | Ayers et al. | |
| 5,733,634 A | 3/1998 | Karel | |
| 5,734,800 A | 3/1998 | Herbert et al. | |
| 5,776,307 A | 7/1998 | Ampulski et al. | |
| 5,795,440 A | 8/1998 | Ampulski et al. | |
| 5,814,190 A | 9/1998 | Van Phan | |
| 5,817,377 A | 10/1998 | Trokhan et al. | |
| 5,846,379 A | 12/1998 | Ampulski et al. | |
| 5,855,739 A | 1/1999 | Ampulski et al. | |
| 5,858,514 A | 1/1999 | Bowers | |
| 5,861,082 A | 1/1999 | Ampulski et al. | |
| 5,865,950 A | 2/1999 | Vinson et al. | |
| 5,871,887 A | 2/1999 | Trokhan et al. | |
| 5,897,745 A | 4/1999 | Ampulski et al. | |
| 5,904,811 A | 5/1999 | Ampulski et al. | |
| 5,906,161 A | 5/1999 | Kessler | |
| 5,906,710 A | 5/1999 | Trokhan | |
| 5,942,085 A | 8/1999 | Neal et al. | |
| 6,048,938 A | 1/2000 | Neal et al. | |
| 6,033,513 A | 3/2000 | Nakamura | |
| 6,096,412 A | 8/2000 | McFarland et al. | |
| 6,173,646 B1 | 1/2001 | Tanaka et al. | |
| 6,187,138 B1 | 2/2001 | Neal et al. | |
| 6,234,078 B1 | 5/2001 | Kessler | |
| 6,281,269 B1 | 8/2001 | Schut | |
| 6,330,857 B1 * | 12/2001 | Maximovsky ...... B41F 15/0836 101/116 |
| 6,458,211 B1 * | 10/2002 | Wefers ................ B41F 15/0836 101/119 |
| 6,477,948 B1 | 11/2002 | Nissing et al. | |
| 6,610,131 B2 | 8/2003 | Harris et al. | |
| 6,651,560 B2 * | 11/2003 | Neuhaus .................. B41M 1/10 101/114 |
| 6,993,964 B2 | 2/2006 | Franz et al. | |
| 7,611,582 B2 | 11/2009 | McNeil et al. | |
| 7,703,394 B2 * | 4/2010 | Neuhaus ................ B41F 31/08 101/350.1 |
| 8,163,132 B2 | 4/2012 | Kien | |
| 8,943,957 B2 | 2/2015 | McNeil et al. | |
| 9,102,182 B2 | 8/2015 | McNeil et al. | |
| 2006/0008514 A1 | 1/2006 | Koenig et al. | |
| 2006/0201630 A1 | 9/2006 | Puffe | |
| 2010/0126366 A1 | 5/2010 | Kasper et al. | |
| 2010/0206221 A1 | 8/2010 | Branca | |
| 2012/0222568 A1 | 9/2012 | Byrne et al. | |
| 2015/0343480 A1 | 12/2015 | Byrne et al. | |

FOREIGN PATENT DOCUMENTS

| | | |
|---|---|---|
| EP | 1 673 225 B1 | 8/2008 |
| GB | 1176321 | 1/1970 |
| GB | 1241793 | 8/1971 |
| GB | 1241794 | 8/1971 |
| GB | 1350059 | 4/1974 |
| GB | 1396282 | 6/1975 |
| GB | 1439458 | 6/1976 |
| GB | 1468360 | 3/1977 |
| GB | 1570545 | 7/1980 |
| GB | 2314292 | 12/1997 |
| WO | WO 84/00516 | 2/1984 |
| WO | WO 99/54143 | 10/1999 |

OTHER PUBLICATIONS

All Office Actions and references listed in U.S. Appl. Nos. 13/040,287; 13/040,290; 13/040,293; 13/040,299; 13/040,311; 13/040,315; 13/040,320; 13/040,333; 13/040,345; 13/040,357; 13/040,375; 13/040,386; 13/040,402; 13/040,419; 13/040,438; 13/040,447; 13/040,467.

PCT International Search Report for 13364 dated Sep. 9, 2015—5 pages.

PCT International Search Report for 14089 dated Feb. 15, 2017—68 pages.

* cited by examiner

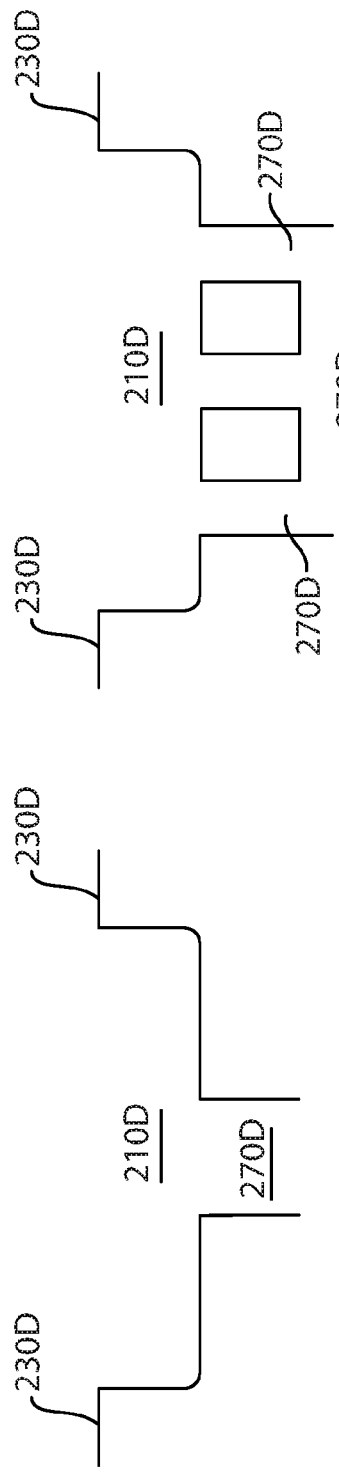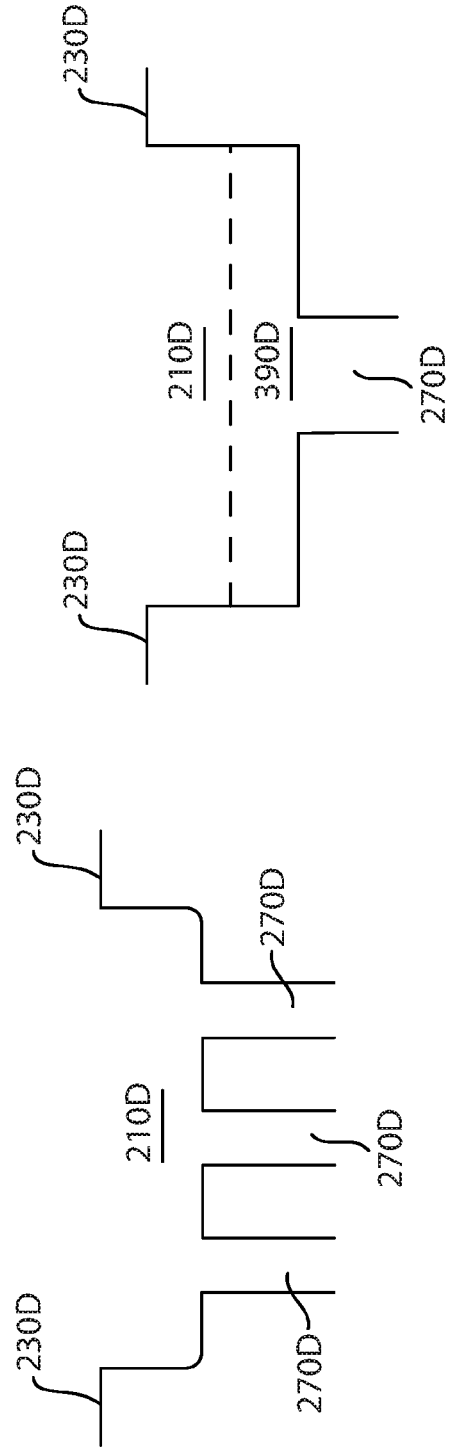

APPARATUS FOR NON-CONTACT PRINTING OF ACTIVES ONTO WEB MATERIALS AND ARTICLES

FIELD OF THE DISCLOSURE

The present disclosure relates to an apparatus and process for disposing actives and other flowable materials, such as adhesives, onto permeable and impermeable web materials, articles (such as absorbent articles), and/or release papers. The disclosure also relates to articles obtainable by such a process and equipment specifically designed for the process.

BACKGROUND OF THE DISCLOSURE

Absorbent articles such as sanitary napkins, panty liners, catamenials, incontinence inserts, and/or diapers for adults or babies are commonly provided with an adhesive on their garment-facing surface to facilitate attachment during their usual usage period to a garment of the user. The usual adhesive may be, for example, a pressure sensitive, hot melt, adhesive. These adhesives are typically covered by a release paper or strip prior to use.

Additionally, such absorbent articles can be constructed with adhesive areas that are used to combine the components that ultimately make up part or the whole of the absorbent article. In particular, multi-layer structures forming the topsheet, core, or back-sheet are often combined by adhesives called construction adhesives.

Typically these absorbent products are made by highspeed machinery. Current machinery includes equipment, such as spray guns or slot coaters that continuously or intermittently add a fluid, such as an adhesive, onto the surface of an absorbent article. Any placement of such a fluid must be done quickly in order to provide high-speed production.

However, current equipment is either inflexible, inaccurate, or both relative to the deposition of the fluid onto the article into the desired pattern of the fluid (adhesive).

For example, hollow drum screen-printing can provide for the creation of a pattern in the screen that can allow for the creation of a desired adhesive pattern. However, adhesive screen-printing is restricted in providing an even, full surface adhesive coverage due to the maximum aperture dimensions and total open area of the a screen relative to the stability of the fluid to be applied.

Other methods can incorporate the use of a gravure, or gravure-like, printing roll. An exemplary gravure printing roll process provides for the rotation of the gravure roll having gravure cells, or indentations disposed upon the outer surface thereof, through a bath containing the fluid (adhesive) which is then placed in contacting engagement with the surface of an absorbent article. The fluid is then transferred to the article from each gravure cell. As mentioned, the gravure roll can contain a specific or desired pattern of cavities upon the surface thereof. Excess fluid placed upon the surface of the gravure roll can be removed by the use of a doctor (i.e., scraper) blade.

While a gravure roll printing process can allow for the application of fluids such as adhesives in patterns on surfaces, the process still has a number of problems associated with it. When applying an adhesive, the gravure roll is continuously supplied with adhesive from an adhesive bath into which the roll is partially submerged and in which it is rotated. Typically, the adhesive must be supplied in a large excess to allow the print roll to rotate through the adhesive bath and become coated with the adhesive. This requires a large amount of energy to be expended particularly in order to maintain the bath and adhesive at the required temperature. Moreover, the rotation of the roll within the bath causes the formation of air bubbles within the adhesive bath that result in the formation of foam. This foam is subsequently transferred to the gravure roll and results in the uneven distribution of the adhesive on the gravure roll surface. This results in the foam-riddled adhesive to consequently be disposed onto the substrate, even after scraping. Furthermore, the foam also collects on the scraper itself and is not readily removable or removed.

Another problem with such a gravure roll printing process is that the amount and distribution of fluid (adhesive) that is deposited from the print roll onto the substrate is extremely difficult to control, resulting in a highly inefficient process. Also, the amount of stringing (i.e. fiberization) of the adhesive during the transfer from the gravure roll to the substrate surface is very large. This results in an irregular application of the adhesive to the surface, in addition to contamination of the adhesive pattern itself. It is believed that it would be beneficial to control a reproduceable application of fluid (e.g., adhesive) from a gravure roll cavity onto a web material or article proximate to a surface thereof.

Some processes could utilize a spraying tool, slot coater, or a series of metering rolls positioned at the right or left hand side of the gravure roll in place of the bath. Such a process continuously applies an amount of adhesive onto a gravure printing roll surface, such that the cavities diposed upon the surface of the gravure roll are filled only to a certain extent. A doctor blade may also be provided to remove any excess adhesive.

Even using the aforementioned adhesive application systems with or without a doctor blade to remove excess adhesive, it has been found that it is difficult to apply sticky, stringy, and viscous adhesives with the precision necessary to provide all cavities of the gravure roll with the required amount of adhesive (e.g. if the volume of all cavities is the same, such that each cavity contains an equal amount of adhesive). This is in particularly the case when the process is performed at a high speed, such as normally necessary in economically feasible production processes, e.g. of more than 20 m/min, or even more than 100 m/min or even more than 150 m/min.

Furthermore, these also require the adhesive to be heated to very high temperatures to be able to spray it onto the surface of a gravure roll, and that the temperature of the adhesive and the roll (or the difference between these temperatures) is difficult to control. Also, slot coaters typically cause the applied adhesive to clump together, seeking to minimize surface area. This results in an uneven application of the fluid to the surface of the gravure roll. Furthermore, the adhesive applied by a slot coater tends to 'fly off' the surface of a rotating gravure printing roll after application, especially when the applied adhesive clumps together and/or when they are very hot and more viscous.

Therefore, there exists a clear need to provide an improved (continuous) high speed process to apply fluids (e.g., adhesive) materials to articles in a manner that overcomes the problems associated with the processes discussed supra. There is a clear need to provide a more accurate and efficient way to apply materials including adhesives onto articles, typically in a shaped design to the surfaces of assembled articles from the surface of an exemplary gravure roll. Such a process should allow for the more uniform application of a fluid, either in the form of a uniform layer, or in the form of dots, which have uniformity in the amount of active per dot. Furthermore, such a process should result in a significantly reduced level of contamination by stringing of the viscous material. This can help ensure that the adhesive or other active material is applied exactly as required. Finally, such a process should provide an article with a much more uniformly applied layer or (dot) pattern of the fluid upon the surface of the article.

Additionally, it is believed that there is a need to eject fluid from a gravure roll to minimize any cohesive forces disposed between the surfaces of the fluid and the gravure roll in order to reduce any effects of stringing (i.e. fiberization) of the adhesive during transfer from the gravure roll to a substrate surface.

SUMMARY OF THE DISCLOSURE

The present disclosure provides for an apparatus for providing non-contact application of fluids onto web materials and articles. The apparatus comprises a gravure roll having a hollow rotating shell having a plurality of cavities disposed within the outer surface thereof and a stationary cylindrical core having a central bore and a channel disposed therein. The central bore is disposed about an axis of the stationary cylindrical core. The channel is in fluid communication with the central bore and in fluid communication with a surface of the stationary cylindrical core. The channel has a single entry point and a single exit point and extends from the central bore to the surface of the stationary cylindrical core. The channel is capable of fluidly communicating a positive pressure from the central bore to the surface of the stationary cylindrical core. The hollow rotating shell is disposed about, and rotatable about, the stationary cylindrical core. Each of the plurality of cavities disposed within the outer surface of the hollow rotating shell are rotated about the stationary cylindrical core and the axis so that a portion of each of the cavities are positioned in contacting and fluid engagement with the channel at the surface of the stationary cylindrical core and the positive pressure is fluidly communicateable from the central bore through the channel and into the cavity from the surface of the stationary cylindrical core. A fluid disposed within a respective cavity of the plurality of cavities disposed within the outer surface of the hollow rotating shell is removed from the respective cavity by the positive pressure when the positive pressure is fluidly communicated from the central bore through the channel and into the cavity from the surface of the stationary cylindrical core.

The present disclosure also provides an apparatus for providing non-contact application of fluids onto web materials and articles. The apparatus comprises a gravure roll having a plurality of cavities disposed within an outer surface thereof and a central bore disposed within the gravure roll. The gravure roll further comprises a plurality of channels disposed therein. Each of the plurality channels is in fluid communication with the central bore and a respective cavity of the plurality of cavities. Each of the channels of the plurality of channels have a single entry point, a single exit point ,and extends from the central bore to the respective cavity of the plurality of cavities. Each channel of the plurality of channels is capable of fluidly communicating a positive pressure from the central bore to the respective cavity of the plurality of cavities. The gravure roll is disposed about, and rotatable about, an axis. The central bore is coextensive with the axis. Each of the plurality of cavities disposed within the outer surface of the gravure roll and the respective channel in fluid communication therewith are rotated about the axis to a position proximate to a roll disposed proximate to the gravure roll so that the positive pressure is fluidly communicateable from the central bore through a respective channel of the plurality of channels and the cavity of the plurality of cavities cooperatively associated thereto and in fluid engagement therewith. A fluid disposed within the respective cavity is removed from the respective cavity by the positive pressure when the positive pressure is fluidly communicated from the central bore through the respective channel and the cavity of the plurality of cavities cooperatively associated thereto and in fluid engagement therewith from the surface of the stationary cylindrical core onto a surface of the roll when the respective cavity is disposed proximate to the surface of the roll.

BRIEF DESCRIPTION OF THE DRAWINGS

FIG. 9 is a partial sectional view of an exemplary surface of an exemplary gravure roll suitable for use with the equipment and process for the non-contact printing of actives onto web materials and articles according to the present disclosure showing a single channel operatively coupled to, and in fluid communication with, a gravure cell;

FIG. 10 is a partial sectional view of another exemplary surface of an exemplary gravure roll suitable for use with the equipment and process for the non-contact printing of actives onto web materials and articles according to the present disclosure showing a plurality of channels operatively coupled to, and in fluid communication with, a gravure cell;

FIG. 11 is a partial sectional view of still another exemplary surface of an exemplary gravure roll suitable for use with the equipment and process for the non-contact printing of actives onto web materials and articles according to the present disclosure showing a single channel operatively coupled to, and in fluid communication with, a plurality of sub-channels that are operatively coupled to, and in fluid communication with, a gravure cell;

FIG. 12 is a partial sectional view of yet another exemplary surface of an exemplary gravure roll suitable for use with the equipment and process for the non-contact printing of actives onto web materials and articles according to the present disclosure showing a single channel operatively coupled to, and in fluid communication with, a reservoir that is operatively coupled to, and in fluid communication with, a gravure cell;

DETAILED DESCRIPTION OF THE DISCLOSURE

Figure 1:
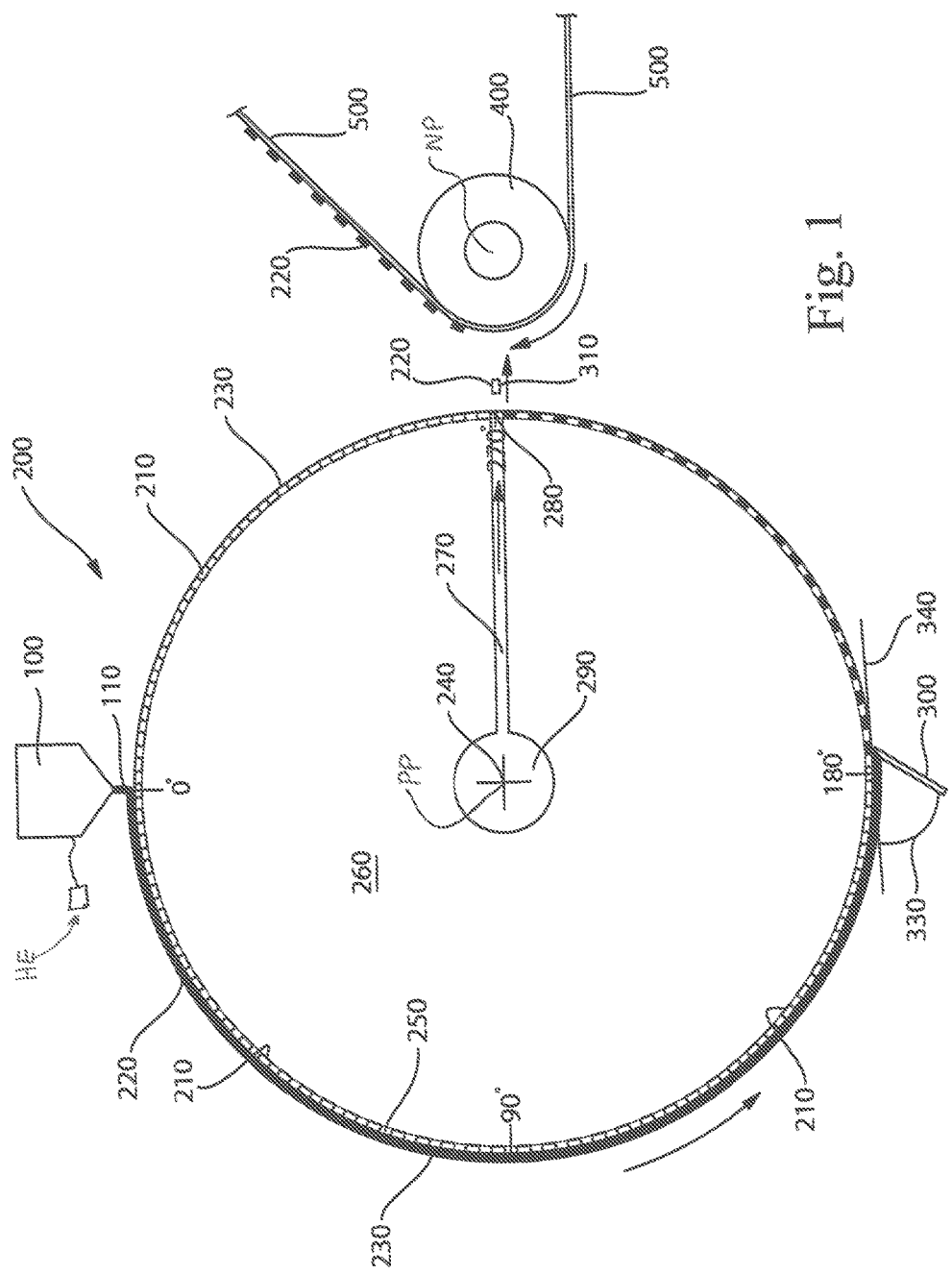
FIG. 1 is a cross-sectional view of exemplary equipment and process for the non-contact printing of actives onto web materials and articles according to the present disclosure.

The process of the present disclosure provide a process for the application of a fluid or other active material, the fluid preferably comprising an adhesive, onto a web material, and/or an article, and/or a series of articles, and/or a web of articles, and/or a (web or series of) absorbent articles, and/or release strip thereof (each individually or collectively referred to herein as a series of articles or web of articles. Such a described process is clearly suitable for the continuous transfer of a fluid material. Therefore, the articles are preferably a continuous series of articles or a web of articles. As used herein, a 'series of articles' means that the articles are distinct and separate. Such a series of articles can be collectively elongate. As used herein, a 'web of articles' means that the articles are connected and are to be separated at a later stage into separate articles. It is envisioned that any fluid applied to such series of articles or web of articles is applied continuously and at a continuous speed onto the surface of an endless, rotating surface (such as a gravure roll) and then continuously and at a continuous speed transferred onto the surface of the series of articles or web of articles.

Without desiring to be bound by theory, it is believed that the process described herein (in particular when the process exhibits the continuous nature discussed supra) has a process speed of at least 20 m/min, more preferably at least 100 m/min, or even at least 150 m/min, or at least about 600 m/min. Without desiring to be bound by theory, it is believed that the process described herein can apply a fluid so that the fluid is applied in high on-dot amounts per surface area, preferably at least 10 $g/m^2$, preferably at least 20 $g/m^2$ or even at least 40 $g/m^2$.

If the fluid is applied in a pattern, the on-dot amount per area is obtained by measuring the amount of fluid applied within a given pattern, excluding any uncovered areas, and subsequently calculating the average amount for the covered areas (and optionally transferred into $g/m^2$). For, example if a desired application pattern provides for 50% of a given surface to be covered with dots of the fluid and 50% is not covered with fluid, then the average weight per area of the total surface is half the on-dot weight per area. If the fluid is applied and covers the whole surface area of an article, the average weight per area of the total surface equals the on-dot area.

The process described herein can utilize a number of different coating devices. In any regard, each different coating device applies a fluid (also called an active material, an adhesive, as well as any similarly descriptive term herein) in the form of a multitude of beads. Essentially, each coating device provides a unit having at least one applicator (in the form of an extruder, spray head, metering rolls, and the like) that is positioned proximate, or in contacting engagement with the external surface of a first tool.

The first tool can be provided as a gravure, or gravure-like roll applicator. As would be understood by one of skill in the art, a gravure roll applicator is a type of intaglio printing process, which involves engraving a desired image onto the surface of a roll applicator (also known in the industry as an image carrier). A gravure roll is created by providing an engraved image that is to be printed through an engraving process that creates pockets (i.e., cells, cavities, indentations, etc.) on the cylinder surface. These cells will contain the fluid that is to be transferred to the surface to be coated. The depth of the cavities can range from 10 to 500 μM.

As shown in FIG. 1, the coater applicator 100 preferably deposits a fluid 110 (e.g., adhesive, etc.) as a continuous stream or as plurality of discrete beads onto the surface of an engraved gravure roll 200. Preferably, the coater applicator 100 process is continuous and the coater applicator 100 continuously applies the fluid 110, which can form endless beads on the gravure roll 200. The coater applicator 100 can be provided as a unit having a plurality of applicators, for example a plurality of extruders. In one embodiment, the coater applicator 100 can extrude the fluid 110 through a die having a plurality of openings. The coater applicator 100 can be positioned so that gravity can assist the deposition of the fluid 110 upon the surface 230 of gravure roll 200.

The surface of the gravure roll 200 can be coated with a material that provides a contact angle with the fluid 110 of at least 60° or at least 80°If the surface 230 of gravure roll 200 has cavities 210 disposed therein, the coating can be present both in-between adjacent cavities 210 and in the cavities 210. Such materials can include polyfluorinated polymers comprising a compound similar to Teflon, available from DuPont or NF(3), available from Nanosol GmbH.

An intended process of the present disclosure provides is the application of adhesives to absorbent articles. As such, an adhesive can be applied on the back-sheet of an absorbent article or on a protecting release paper, which is removed by the user prior to adhering the absorbent article to a garment. Therefore, the fluid 110 herein may be any material, which is printable. The equipment and process described herein can be very advantageous for the printing of viscous and/or sticky materials. This can include materials that have a peel force of more than 0.1 N/cm, or more than 0.2 N/cm, or more than 0.4 N/cm. This is the peel force of the active material when applied in an average base weight of 20 g/cm² on a surface, as described infra. Of course, the fluid 110 can be applied in different amounts upon articles or webs as described infra. The fluid 110 can be provided with an elastic modulus G' at 20° C. of less than 100,000 Pa, or less than 50,000 Pa, or less than 20,000 Pa. The fluid 110 can have an elastic modulus G' that increases from 10 to 10,000 Pa in less than 60° C, or less than 40° C, or less than 30° C, or less than 20° C., or less than a 10° C. temperature range where the transition happens when the fluid 110 passes from a melted state to a solid state. A suitable material for fluid 110 can have a loss tangent tan δ (G"/G') at 20° C. of more than 0.5, or more than 1.0, or more than 1.5. Further, a suitable material for fluid 110 can have a surface energy σ at 20° C. of less than 35 mN/m, or less than 25 mN/m. Fluid 110 can have a viscosity of more than 100 mPa·s, or more than 200 mPa·s, and preferably less than 5000 mPa—s, or less than 2500 mPa·s, or less than 1500 mPa·s, or less than 1000 mPa·s or less than 800 mPa·s at process temperature. The fluid 110 can be solid at 20° C.

Hot melt adhesives can be particularly useful. Hot-melt adhesives can generally comprise a thermo-plastic base material, tackifying resin(s), mineral oils, waxes, or a mixture thereof. Hot melt adhesives can have a minimum melting temperature of about 80° C. or about 100° C. In any regard, hot melt adhesives should maintain adhesive performance until disposal of the disposable absorbent article. Adhesives can include LAX307NE and LAX3013NE (available from Savare'), Lunatack BD160 (available from Fuller), and National 134593A (available from National Starch). Other fluids 110 suitable for use by the apparatus and process of the present disclosure can include hydrophobic agents, lotions, surfactants, and antimicrobials.

The coater applicator 100 can be positioned at any point along the periphery of gravure roll 200. In the embodiment shown in FIG. 1, coater applicator 100 is positioned at the top of the gravure roll 200 and by convention only, at 0°. However, one of skill in the art could position coater applicator 100 between 45° and 315°, preferably 10° and 350°, or thus at 0°.

In one embodiment, the coater applicator 100 can apply more than 2 beads onto the surface 230 of gravure roll 200, typically at least 4 or even at least 5 or even at least 8, or even at least 12. The exact amount of fluid 110 deposited upon the surface 230 of gravure roll 200 can depend on the width of the gravure roll 200, the viscosity of the fluid 110 during application upon the surface 230 of gravure roll 200, and/or the spreadability of the fluid 110 by the coater blade 300 upon the surface 230 of gravure roll 200.

Preferred may be that the pitch (the shortest distance between the middle of one bead of fluid 110 to the middle of a next bead of fluid 110 disposed upon the surface 230 of gravure roll 200, in direction of the width of the gravure roll 200, is less than 20 mm, preferably less than 15 mm, or even less than 10 mm, or even less than 5 mm, but preferably more than 100 microns, or even more than 500 microns.

In one embodiment, the openings of the applicators forming coater applicator 100 can have any shape. Therefore, the openings can be round, square, diamond-shaped, rectangular, triangular, and combinations thereof.

The coater applicator 100 is preferably heated by a heating element HE with a heat control, to ensure a constant temperature of the fluid 110 that is applied by the coater applicator 100 to the surface 230 of gravure roll 200. Preferred may be that the fluid 110 is for example applied at a temperature of between 70° C. and 250° C. or even 200° C., or even 80° C. to 19020 C. or even to 170° C., or even 10020 C. or even 11020 C. to 16020 C. The exact temperature can depend upon the (temperature-dependent) viscosity profile and/or elasticity profile of the fluid 110 applied in the process or with the equipment of the present disclosure.

A pressure can be applied to the coater applicator 100, as would be understood by those of skill in the art in extrusion processes, such that the fluid 110 exits the coater applicator 100 aided by this pressure. For example, the coater applicator 100 can be provided an unit containing active material to be applied, which is under a certain pressure and which forces the fluid 110 through the individual openings, e.g. through a die with openings, or a through individual applicator tubes of coater applicator 100. An applied pressure can also beneficially aid in the application of the required amount of fluid 110 per surface area of the gravure roll 200. One of skill in the art would understand that the pressure applied to the coater applicator 100 can be adjusted if the surface speed of gravure roll 200 changes.

In one embodiment, the coater applicator 100 is can be provided in a fixed position and/or orientation with respect to the surface 230 of gravure roll 200. In such a position and/or orientation, the coater applicator 100 can apply a constant, continuous amount of fluid 110 onto the surface 230 of gravure roll 200. Alternatively, a coater applicator 100 provided with a reciprocal movement (i.e., a reciprocating motion) could be used in certain applications, where for example, an intermittent supply of the fluid 110 is required by the cavity pattern disposed upon the surface 230 of gravure roll 200.

The gravure roll 200 of FIG. 1 can be provided with any dimension required for the process required. It is preferably a gravure roll 200 having an endless surface, and thus suitable as a rotatable/rotating tool. One embodiment of gravure roll 200 can be provided in the form of a rotatable belt, however gravure roll 200 is typically provided as a cylindrical roll. The rotatable gravure roll 200 can rotate with any required surface speed. Exemplary surface speeds of gravure roll 200 are at least 10 m/min, 100 m/min, or more. In this regard, the length of the surface 230 of gravure roll 200 (i.e., the length of one rotation of gravure roll 200) and the diameter of the gravure roll 200 and the surface speed of the gravure roll 200 can be adjusted as required by one of skill in the art as may be required by the process. Exemplary gravure roll 200 diameters may be within the range of 50 mm and 3000 mm, or 100 mm and 800 mm.

The gravure roll 200 can be provided with any width. A desired width can depend on the size of the articles to be coated with the fluid 110 or even the number of articles to be coated with the fluid 110 simultaneously.

Typically, the gravure roll 200 is provided as a roll and the coater applicator 100, coater blade 300 and roll 400 are positioned orbitally about the gravure roll 200. In one embodiment, coater applicator 100 is positioned proximate to the top of gravure roll 200, coater blade 300 is disposed past the lowest position of the gravure roll 200 (as seen in the direction of rotation of the gravure roll 200) and the roll 400 past the coater blade 300, as described infra.

As shown in FIG. 1, an exemplary gravure roll 200 is preferably a gravure or gravure-like printing roll that has cavities 210 (also referred to herein as cells, gravures, and the like) disposed within its surface 230. The cells 210 serve to receive the fluid 110. The gravures or cavities 210 can have any dimension. However, it should be understood that the cavities 210 can be provided with a pitch that can be less than the pitch of the beads applied onto the surface 230 of gravure roll 200 by coater applicator 100. In one embodiment the pitch can be less than 2 mm, or less than 1 mm. In one embodiment, the width or diameter of a single cavity 210 ranges from 0.1 to 1.8 mm. The cavities 210 can be provided with a depth that ranges from 10 to 500 microns. The surface of the gravure roll 200 is preferably coated with a material that provides a contact angle with the fluid 110 of at least 60°, or at least 70°, or at least 80°.

In one embodiment, if the gravure roll 200 is provided with cavities 210 disposed upon the surface thereof, fluid 110 can be present both between adjacent cavities 210 and within cavities 210.

The gravure roll 200 can be heated by the incorporation of a heating element and a temperature control. Providing heat to gravure roll 200 can ensure that the fluid 110 remains at a desired temperature while disposed upon the surface 230 of gravure roll 200. If desired, the temperature of fluid 110 can be provided within a desired range of the desired target temperature, typically within 5° C. Gravure roll 200 can be provided with a temperature so that the gravure roll 200 or at least the surface 230 of gravure roll 200 has a temperature that is at least 5° C., or at least 10° C., or at least 20° C. higher than the temperature of the fluid 110 leaving the coater applicator 100 (and thus typically the temperature of the coater applicator 100 when initially applied to the surface 230 of gravure roll 200). When used herein, the 'process temperature' means this temperature of the surface 230 of gravure roll 200.

Without desiring to be bound by theory, it is believed that the described process and equipment is fully capable of ejecting a fluid from a cavity disposed upon the surface of a gravure roll thereby minimizing any cohesive forces disposed between the surfaces of the fluid and the gravure roll. Without desiring to be bound by theory, it is believed that this can reduce any effects of stringing (i.e. fiberization) of the adhesive during transfer from a cavity disposed upon the surface of a gravure roll to a substrate surface. One way to accomplish this desired result that would be understood by one of skill in the art would be to provide an ejection force (in the form of positive pressure to a respective cavity that exceeds the adhesive forces disposed between the cavity and fluid disposed therein. Additionally, it is believed that one of skill can further reduce any cohesive forces between the surfaces of the fluid and the surface of the gravure roll by further reducing the surface energy of the surface of the gravure roll and any cavity disposed thereon.

Figure 2:
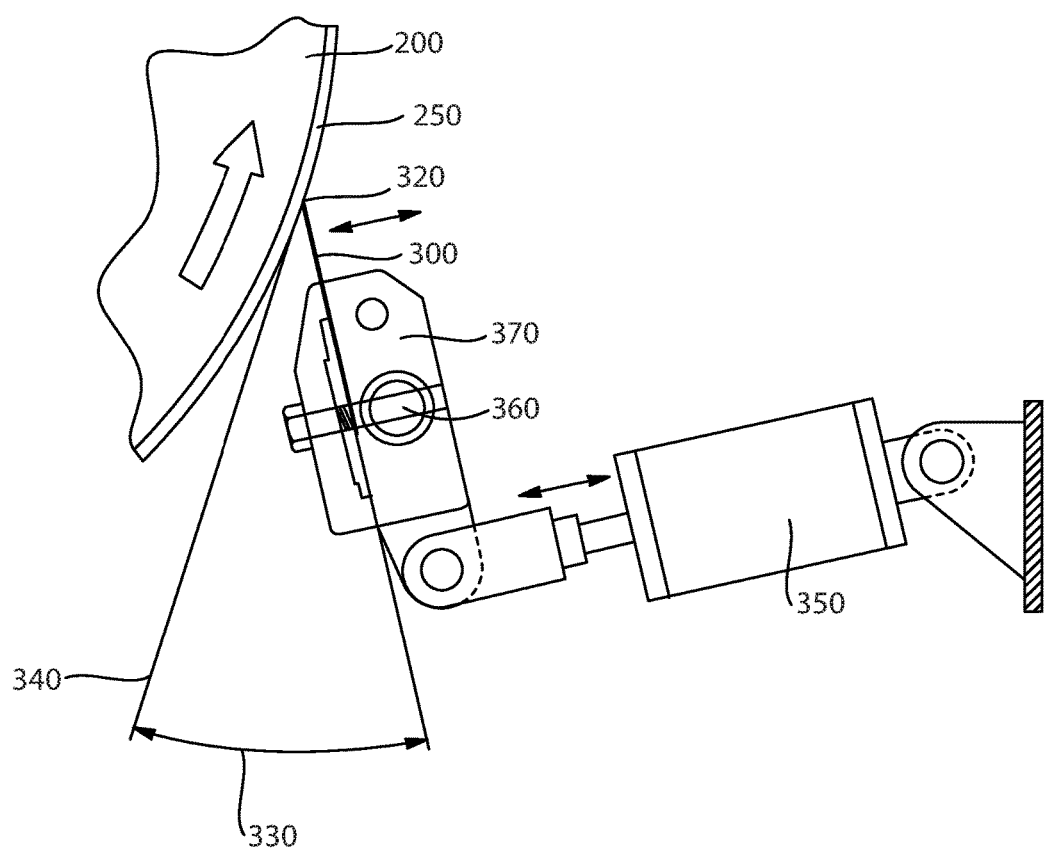
FIG. 2 Is a perspective view of an exemplary coater blade and adjustment mechanism according to the present disclosure.

As shown in FIGS. 1 and 2, the surface 230 of shell 250 of gravure roll 200 can contacted with a coater blade 300. The coater blade 300 can contact the surface 230 of shell 250 of gravure roll 200 so that the angle 330 of the coater blade 300 and the tangent 340 of the shell 250 at the point of contact 320 with shell 250 is between 4 degrees and 45 degrees, or between 15 degrees and 30 degrees. The pressure exerted by the coating blade 300 onto the shell 250 can be kept constant, by use of an air piston 350 connected to a pivot 360 that connects to the blade 300 via a bracket 370. The coater blade 300 spreads out the extruded fluid 220 (not shown in FIG. 2 but see FIG. 1) and also pushes the extruded fluid 220 into the cavities disposed within shell 250 of gravure roll 200 (not shown in FIG. 2, but see FIG. 1).

The angle between the tangent of the gravure roll 200 (i.e., a line perpendicular on the axis of the gravure roll 200) and the coater blade 300 can range from between 5° and 40°, or between 1020 and 35°, or between 15° and 30°. If the gravure roll 200 is moving (e.g., rotating about axis 240) coating blade 300 does not move. When gravure roll 200 is moving, the angle of coater blade 300 relative to gravure roll 200 is the angle disposed between the tangent and the coating blade 300 on the side where the gravure roll 200 is moving from, e.g. the opposite side to the direction of motion. It should be understood that the angle of the coater blade 300 relative to gravure roll 200 can be between the tangent and only the portion of the coater blade 300 that is in contact with the surface 230 of gravure roll 200, or between the tangent and the coater blade 300 as a whole. For example, the coater blade 300 may be provided with a bent top portion and only this top portion has the above-defined angle relative to the the tangent of the surface 300 of gravure roll 200. In one embodiment, the coater blade 300 is linear and that the blade as a whole has the above defined tangent angle relative to the surface 230 of gravure roll 200.

For a curved gravure roll 200, typically a cylinder or roll, this angle is the angle between the coating blade 300 and the tangent line relative to the surface 230 of gravure roll 200. This tangent line is generally understood to be the line grazing the curved surface of the gravure roll 200 at the point of contact with the coating blade 300 and perpendicular on the radius of the gravure roll 200. If the surface of the gravure roll 200 is flat, the tangent is the surface of the gravure roll 200.

The coater blade 300 can be provided to provide a constant pressure upon the surface 230 of the gravure roll 200. The coater blade 300 can apply a constant pressure or force/length on the surface 230 of at least 600 N/m, or at least 700 N/m, or even 1000 N/m. Additionally, the coating blade 300 can be operably connected to a unit which that control the force/length provided by coater blade 300 upon the surface 230 through the use of a pivot or spring.

The length of the coater blade 300 can vary as required by the process. However, one of skill in the art would understand that it may be beneficial to keep the coating blade 300 relatively short, for example from 1 to 20 cm, or even 5 to 15 cm, in length to provide a more accurate and/or constant force/length is applied on the gravure roll 200. Further, when the gravure roll 200 is provided as a roll, the coating blade 300 can be positioned past the lowest point of the gravure roll 200, seen from the direction of rotation of the gravure roll 200. Any excess fluid removed from the surface 230 by coating blade 300 can be recycled for re-use in the coating process and/or removed from the process as may be required by the application and/or upon the presence of any contamination present in extruded fluid 220.

Referring again to FIG. 1, gravure roll 200 can be provided as a shell 250. The shell 250 can be provided with a plurality comprising any number of cavities 210 that each form a passage between the inner and outer surfaces of the shell 250. These cavities 210 may be arranged either to form a pattern which is to be printed onto the web material or article 500, or may be arranged at random so as to give a variegated, spotted or mottled effect. The size and the spacing of the cavities 210 can be placed upon the surface 230 by placing rows of groups of cavities 210 sufficiently close together to form continuous lines or patches.

Disposed within the shell 250 is a stationary cylindrical core 260. Stationary cylindrical core 260 can be separated from the shell 250 by a sheet of polytetrafluorethylene (P.T.F.E.) which serves the dual purpose of forming a bearing or bearing surface for the shell 250, and providing a sealing material to assist in preventing the seepage of fluid 110 between the shell 250 and the stationary cylindrical core 260. In one embodiment, the sealing material can surround the stationary cylindrical core 260 except for a narrow gap 280 extending parallel to the axis 240 of the gravure roll 240 and the stationary cylindrical core 260. The gap 280 coincides with a row of radially disposed cavities 210 disposed within the shell 250 and communicating with a central bore 290. Central bore 290 can be coextensive with the axis 240 or disposed about axis 240 and is provided in fluid communication with a source of positive pressure PP.

The source of positive pressure can be driven by a metering pump driven at a speed proportional to that of the rotation speed of surface 250. Thus the rate at which positive pressure is supplied to the manifold formed by the central bore 290, channel 270, and gap 280 is proportional to the rotational velocity of shell 250, roll 400, or web material or article 500 by varying the relationship between the speed of the metering pump and the surface 230 speed, the exit velocity of a fluid 100 disposed within a cavity 210 can readily be adjusted.

As the shell 250 rotates about axis 240 of gravure roll 200, the cavities 210 are each brought successively in register with the channel 270, which is arranged so that the outer end of the cavities 250 are adjacent that region of the roll 400 which is in contact with the web material or article 500 disposed thereabout. Alternatively, roll 400 may not be required and/or used by the process. In such a case a web material or article 500 can be directly positioned proximate to surface 230 at any desired angle relative to surface 230 of gravure roll 200. In this case, as the shell 250 rotates about axis 240 of gravure roll 200, the cavities 210 are each brought successively in register with the channel 270, which is arranged so that the outer end of the cavities 250 are adjacent the web material or article 500.

As a result, as the shell 250 rotates about axis 240 and stationary cylindrical core 260, positive pressure is injected through the channel 270 from central bore 290 through gap 280 and into each cavity 210 thereby displacing any extruded fluid 220 disposed therein (either in the form of a droplet or aggregation 310) onto web material or article 500 in a pattern determined by the arrangement of the cavities 210. Roll 400 can be positioned so that the web material or article 500 rotates around the roll 400 with an exit angle between 3020 and 70° or between 32° and 4520. Further, roll 400 can be connected to or comprise a source of negative pressure NP, such as vacuum means, such as a vacuum pump or chamber, operably connected to a surface of the roll 400 so that the roll 400 motivates the droplet or aggregation 310 of fluid 110 and/or web material or article 500 on or toward roll 400 during rotation.

The size and depth of the imprint formed by each injection through a cavity 250 onto the web material or article 500 is determined by the amount and pressure of the positive pressure metered through central bore 290 into channel 270 and gap 280 into a respective cavity 210 relative to the speed of the shell 250, the size of the cavities 210 and the properties of the fluid 110 disposed with each cavity 210. These factors can be mutually adjusted to give a desired result. A consideration to be borne in mind when selecting the diameter of a cavity 210 is that if the shell 250 of gravure roll 200 is operated at a high peripheral speed, there is a danger of fluid 110 being ejected from the cavities 210 at times other than when they are in register with the channel 270 and gap 280. This tendency can be aggravated if the cavities 210 are large. With appropriate sizing of the cavities 210, no problems should arise at any production speed at present contemplated. An advantage of the apparatus is that its speed of operation may be varied over a wide range to suit production requirements or the rate of operation of other apparatus arranged upstream or downstream of it without significantly affecting its performance.

In an alternative construction (not shown), the P.T.F.E. sheet can be omitted, and the roller shell 250 can be formed of nylon or other synthetic plastics material. In yet another variant, the stationary cylindrical core 260 may be formed of nylon or other synthetic plastics material. It should be noted however that where different materials are used for the stationary cylindrical core 260 and for the shell 250, care should be taken to ensure that differential thermal expansion of the two parts does not lead to binding between them.

It should also be understood that while the construction of the stationary cylindrical core 260 described supra is satisfactory for use with shells 250 of relatively small length and diameter, with larger diameter and longer shells 250 a lighter construction for the stationary cylindrical core 260 may be desirable. Since the primary purpose of the stationary cylindrical core 260 is merely to define a manifold through which a source of positive pressure is fluidly communicated from central bore 290, through channel 270, and gap 280 and into cavity 210 disposed within the surface 230 of shell 250 of gravure roll 200, with the secondary function in the embodiment described for providing an additional support for the shell 250, it will be understood that widely differing constructions may be employed as required.

Figure 3:
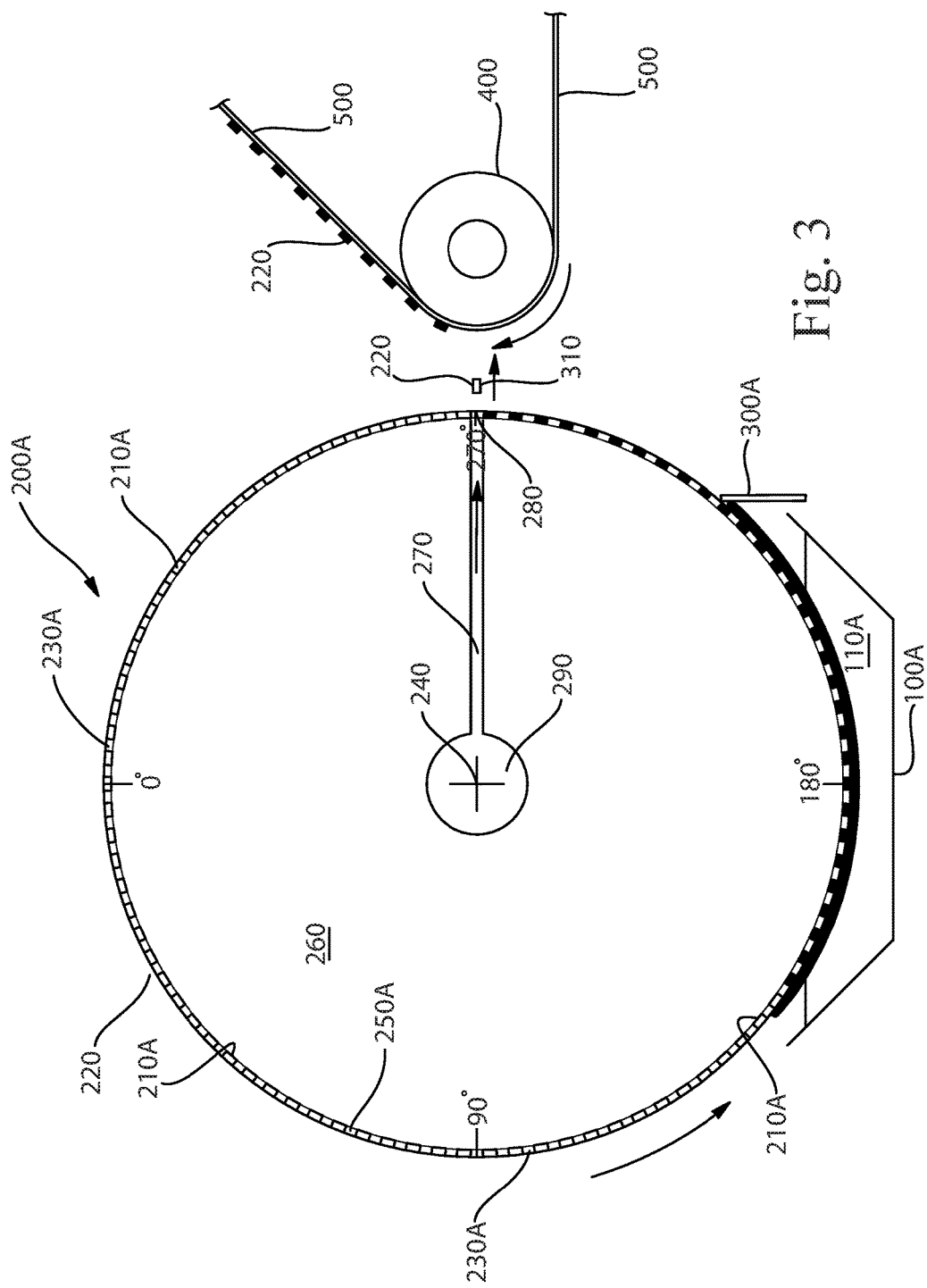
FIG. 3 is a cross-sectional view of another exemplary equipment and process for the non-contact printing of actives onto web materials and articles according to the present disclosure having an exemplary coater applicator.

As shown in FIG. 3, gravure roll 200A can be provided with a coater applicator 100A in the form of a fluid 110A bath. In operation, the gravure roll 200A (namely shell 250A) rotates about axis 240 and stationary cylindrical core 260 through the fluid 110A disposed within coater applicator 100A. The coater applicator 100A applies a fluid 110A, such as an adhesive, onto the surface 230A of the shell 250A of gravure roll 200A so that the fluid 110A is at least disposed within each cavity 210A disposed upon the surface 230A of shell 250A.

The direction of rotation of the shell 250A of gravure roll 200A is indicated and the positions of the coater applicator 100A, coater blade 300A and roll 400 are indicated in degrees of the circle which the cross-section of the gravure roll 200A. The coater applicator 100A shown in FIG. 3 positioned at the bottom of the gravure roll 200A and, for reference purposes only, thus at 180°. The coater can be disposed at any position provided it is before the position of the coater blade 300A and roll 400, in the direction of rotation.

A source of positive pressure is supplied to the manifold formed by the central bore 290, channel 270, and gap 280 as the shell 250A rotates about axis 240 of gravure roll 200A. In turn, each cavity 210A is brought successively in register with the channel 270 and gap 280 so that as the shell 250A rotates about axis 240 and stationary cylindrical core 260, positive pressure is injected through the channel 270 from central bore 290 through gap 280 and into each cavity 210A thereby displacing any extruded fluid 220 disposed therein (either in the form of a droplet or aggregation 310) onto web material or article 500 in a pattern determined by the arrangement of the cavities 210A.

Figure 3A:
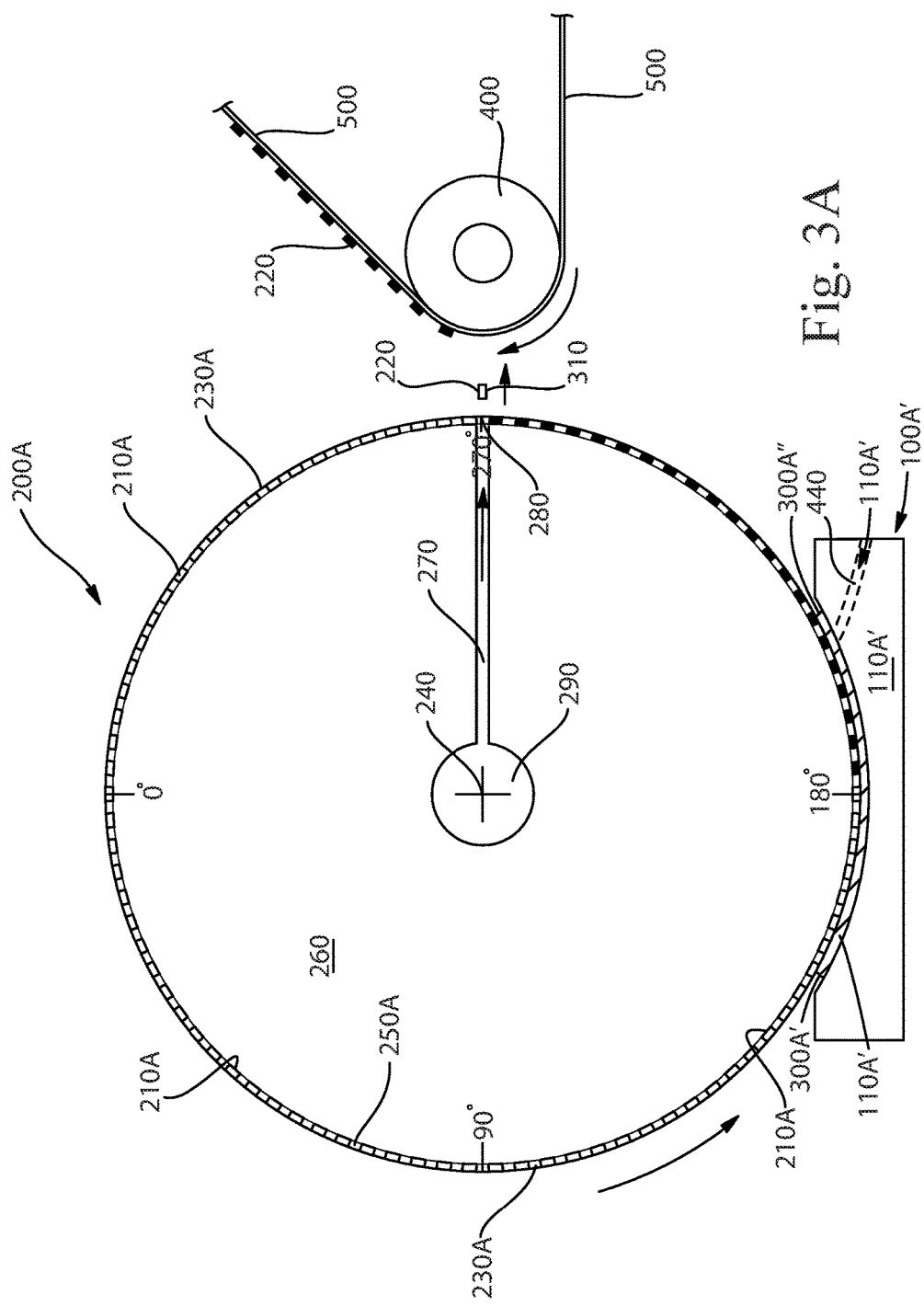
FIG. 3A is a cross-sectional view of still another exemplary equipment and process for the non-contact printing of actives onto web materials and articles according to the present disclosure having another exemplary coater applicator.

As shown in FIG. 3A, gravure roll 200A can be provided with a coater applicator 100A' in the form of a fluid 110A' bath. In operation, the gravure roll 200A (namely shell 250A) rotates about axis 240 and stationary cylindrical core 260 through the fluid 110A' disposed within coater applicator 100A'. Fluid 110A is positioned between gravure roll 200A (namely shell 250A and coater applicator 100A') from a position external to coater applicator 100A' to a position between gravure roll 200A (namely shell 250A) and coater applicator 100A'via passageway 440. The coater applicator 100A' applies a fluid 110A', such as an adhesive, onto the surface 230A of the shell 250A of gravure roll 200A so that the fluid 110A' is at least disposed within each cavity 210A disposed upon the surface 230A of shell 250A.

The direction of rotation of the shell 250A of gravure roll 200A is indicated and the positions of the coater applicator 100A', first coater blade 300A', second coater blade 300A", and roll 400 are indicated in degrees of the circle which the cross-section of the gravure roll 200A. The coater applicator 100A' shown in FIG. 3A positioned at the bottom of the gravure roll 200A and, for reference purposes only, thus at 180 20 The coater 100A' can be disposed at any position provided it is before the position of first coater blade 300A', second coater blade 300A", and roll 400, in the direction of rotation.

A source of positive pressure is supplied to the manifold formed by the central bore 290, channel 270, and gap 280 as the shell 250A rotates about axis 240 of gravure roll 200A. In turn, each cavity 210A is brought successively in register with the channel 270 and gap 280 so that as the shell 250A rotates about axis 240 and stationary cylindrical core 260, positive pressure is injected through the channel 270 from central bore 290 through gap 280 and into each cavity 210A thereby displacing any extruded fluid 220 disposed therein (either in the form of a droplet or aggregation 310) onto web material or article 500 in a pattern determined by the arrangement of the cavities 210A.

Figure 4:
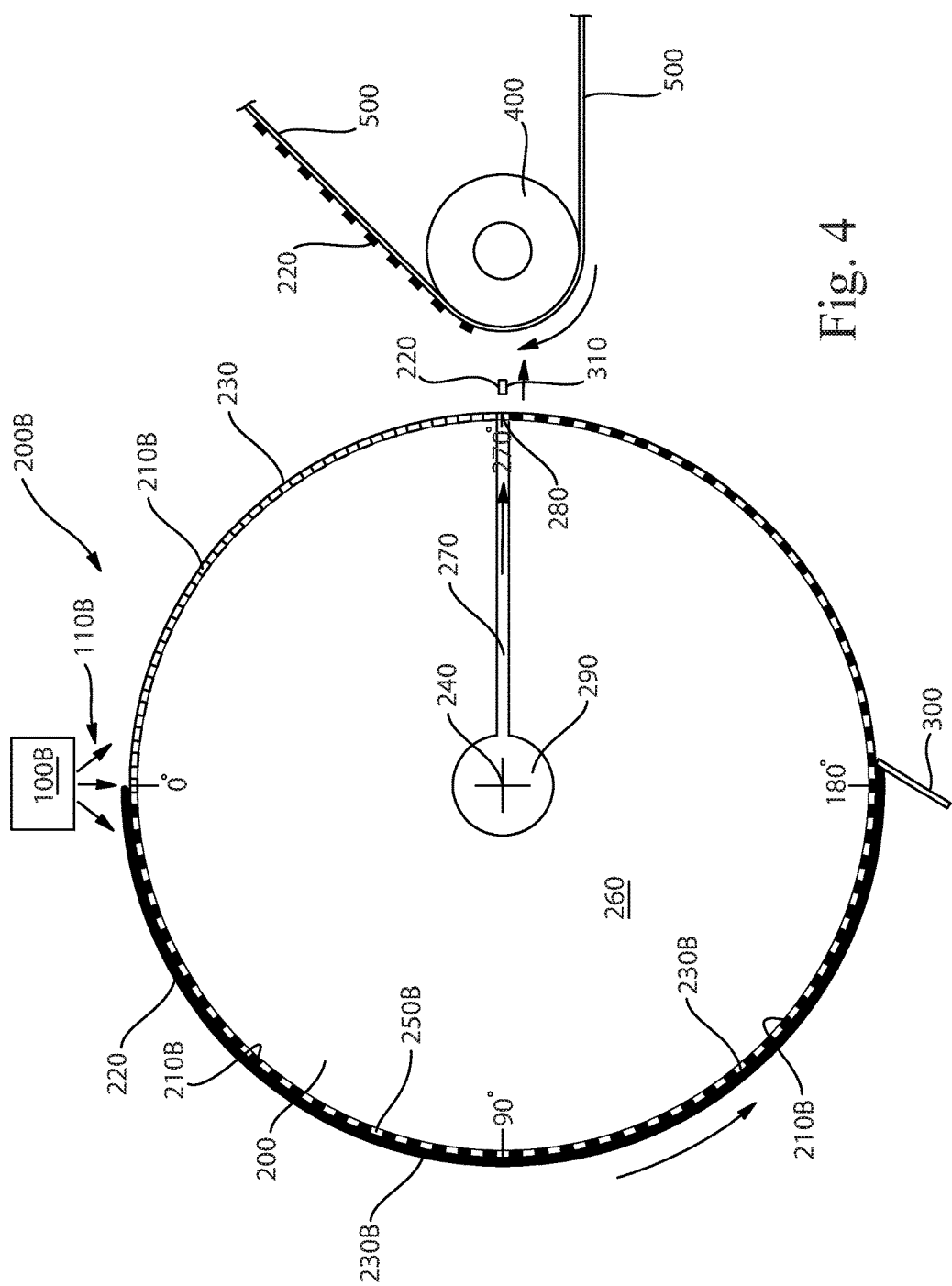
FIG. 4 is a cross-sectional view of yet another exemplary equipment and process for the non-contact printing of actives onto web materials and articles according to the present disclosure.

As shown in FIG. 4, gravure roll 200B can be provided with a coater applicator 100B in the form of a spray applicator 110B. In operation, the gravure roll 200B (namely shell 250B) rotates about axis 240 and stationary cylindrical core 260 through the fluid 110B disposed upon shell 250B by spray applicator 100B. The spray applicator 100B applies a fluid 110B, such as an adhesive, onto the surface 230B of the shell 250B of gravure roll 200B so that the fluid 110B is at least disposed within each cavity 210B disposed upon the surface 230B of shell 250B.

The direction of rotation of the shell 250 of gravure roll 200B is indicated and the positions of the spray applicator 100B, coater blade 300B and roll 400 are indicated in degrees of the circle which the cross-section of the gravure roll 200B. The spray applicator 100B shown in FIG. 4 is positioned at the top of the gravure roll 200B and, for reference purposes only, thus at 0°. It would be realized by one of skill in the art that spray coater 100B can be disposed at any position provided it is before the position of the coater blade 300B and roll 400, in direction of rotation.

As with the embodiments described supra, a source of positive pressure is supplied to the manifold formed by the central bore 290, channel 270, and gap 280 as the shell 250B rotates about axis 240 of gravure roll 200B. In turn, each cavity 210B is brought successively in register with the channel 270 and gap 280 so that as the shell 250B rotates about axis 240 and stationary cylindrical core 260, positive pressure is injected through the channel 270 from central bore 290 through gap 280 and into each cavity 210B thereby displacing any extruded fluid 220 disposed therein (either in the form of a droplet or aggregation 310) onto web material or article 500 in a pattern determined by the arrangement of the cavities 210B.

Figure 5:
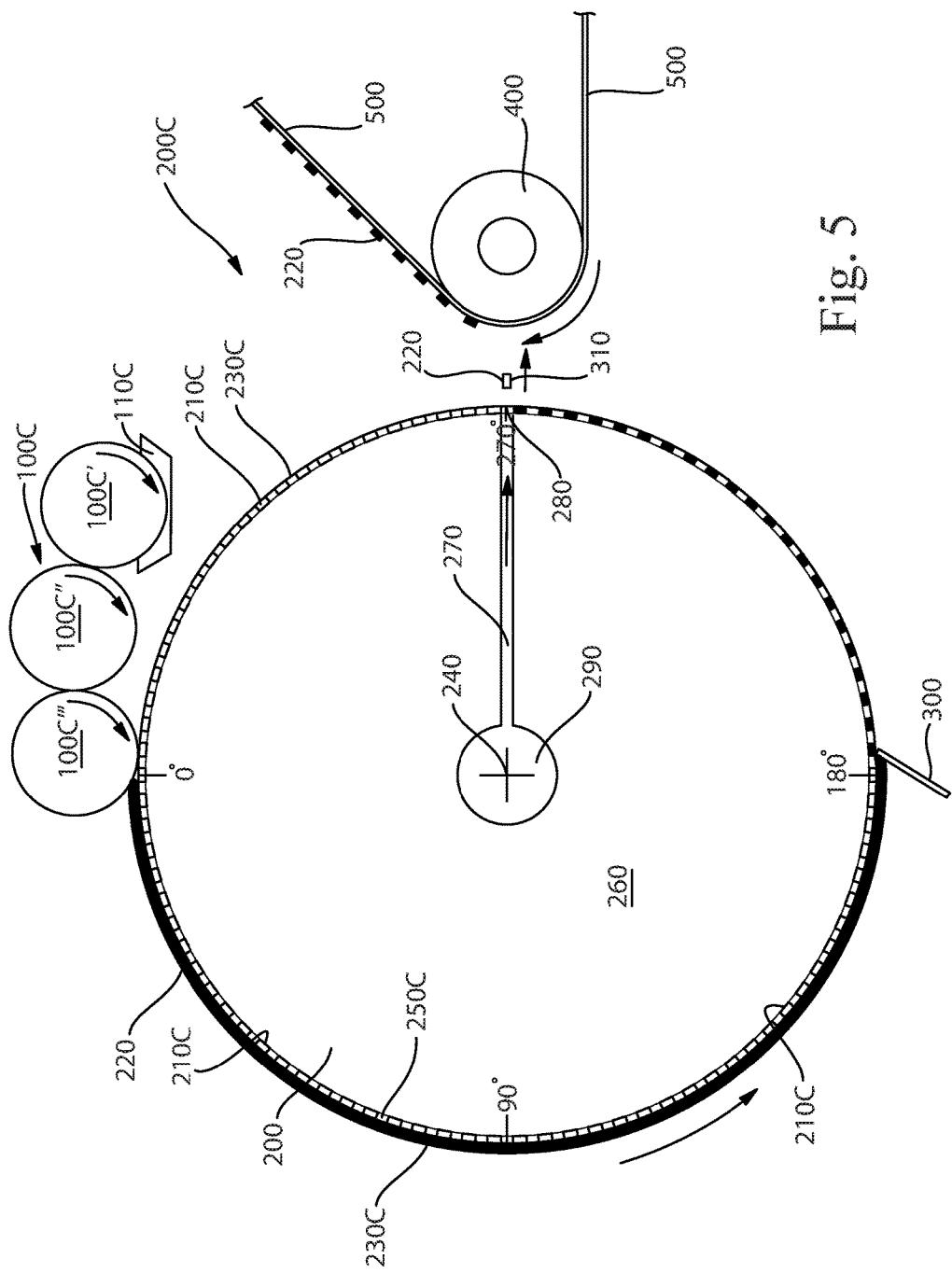
FIG. 5 is a cross-sectional view of still another exemplary equipment and process for the non-contact printing of actives onto web materials and articles according to the present disclosure.

As shown in FIG. 5, gravure roll 200C can be provided with a coater applicator 100C in the form of a series of metering rolls 100C', 100C", and 100C'" (there being no limit on the number of metering rolls present for coater application 100C). In operation, the gravure roll 200C (namely shell 250C) rotates about axis 240 and stationary cylindrical core 260 and is coated with fluid 110C by the last of a series of metering rolls (in the exemplary embodiment provided here—100C'") by coater applicator 100C. The coater applicator 100C applies a fluid 110C, such as an adhesive, onto the surface 230C of the shell 250C of gravure roll 200C so that the fluid 110C is disposed upon the surface of shell 250C and at least disposed within each cavity 210C disposed upon the surface 230C of shell 250C.

As with the embodiments described supra, the direction of rotation of the shell 250C of gravure roll 200C is indicated and the positions of the coater applicator 100C, coater blade 300C, and roll 400 are indicated in degrees of the circle which the cross-section of the gravure roll 200C. The coater applicator 100C shown in FIG. 5 is positioned at the top of the gravure roll 200C and, for reference purposes only, thus at 0°. It would be realized by one of skill in the art that coater applicator 100C can be disposed at any position provided it is before the position of the coater blade 300C and roll 400, in direction of rotation.

A source of positive pressure is supplied to the manifold formed by the central bore 290, channel 270, and gap 280 as the shell 250C rotates about axis 240 of gravure roll 200C. In turn, each cavity 210C is brought successively in register with the channel 270 and gap 280 so that as the shell 250C rotates about axis 240 and stationary cylindrical core 260, positive pressure is injected through the channel 270 from central bore 290 through gap 280 and into each cavity 210C thereby displacing any extruded fluid 220 disposed therein (either in the form of a droplet or aggregation 310) onto web material or article 500 in a pattern determined by the arrangement of the cavities 210C.

Figure 5A:
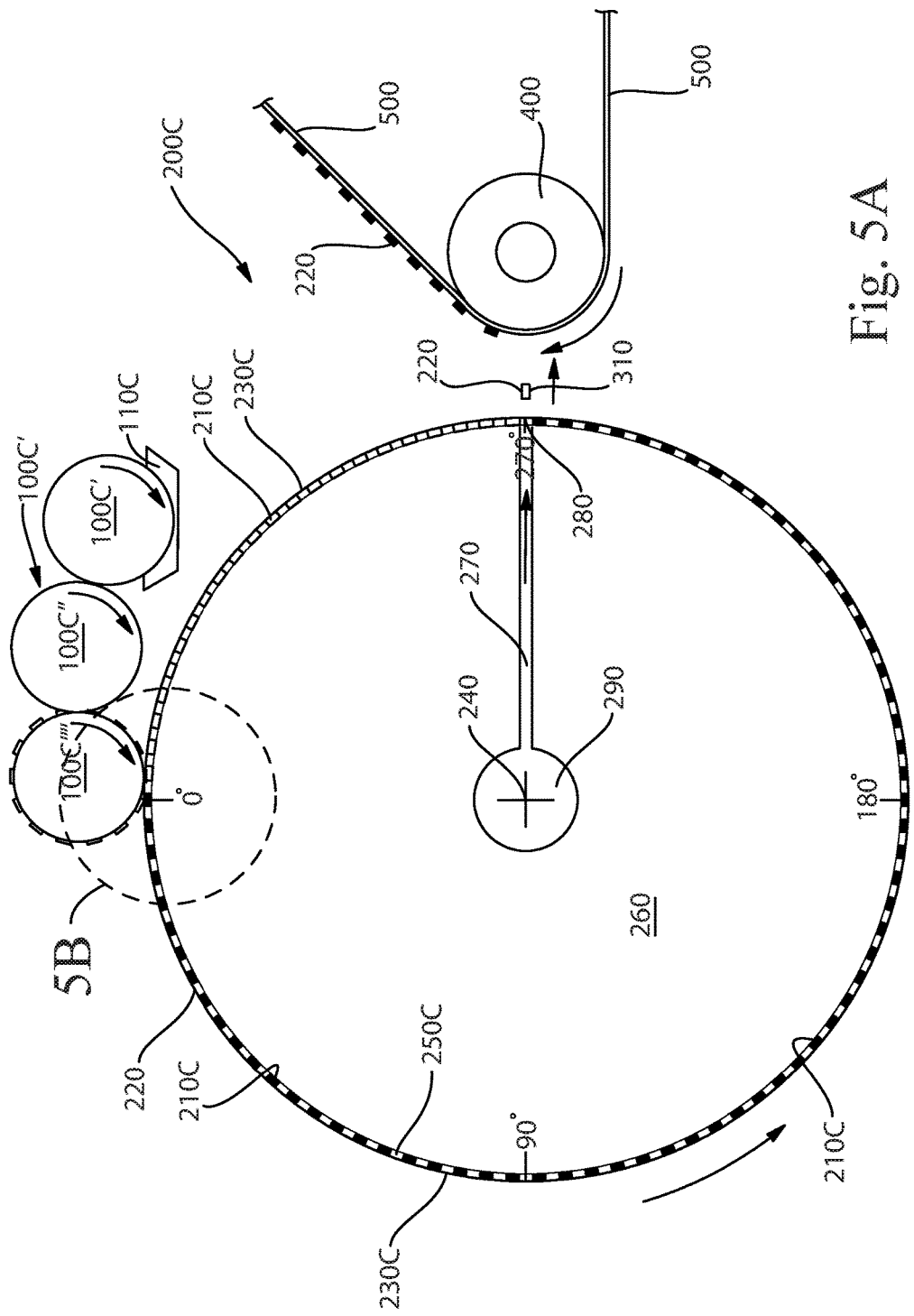
FIG. 5A is a cross-sectional view of still yet another exemplary equipment and process for the non-contact printing of actives onto web materials and articles according to the present disclosure where an exemplary metering roll is provided with an exemplary surface complementary to the pattern of cavities disposed upon the surface of an exemplary gravure roll.
Figure 5B:
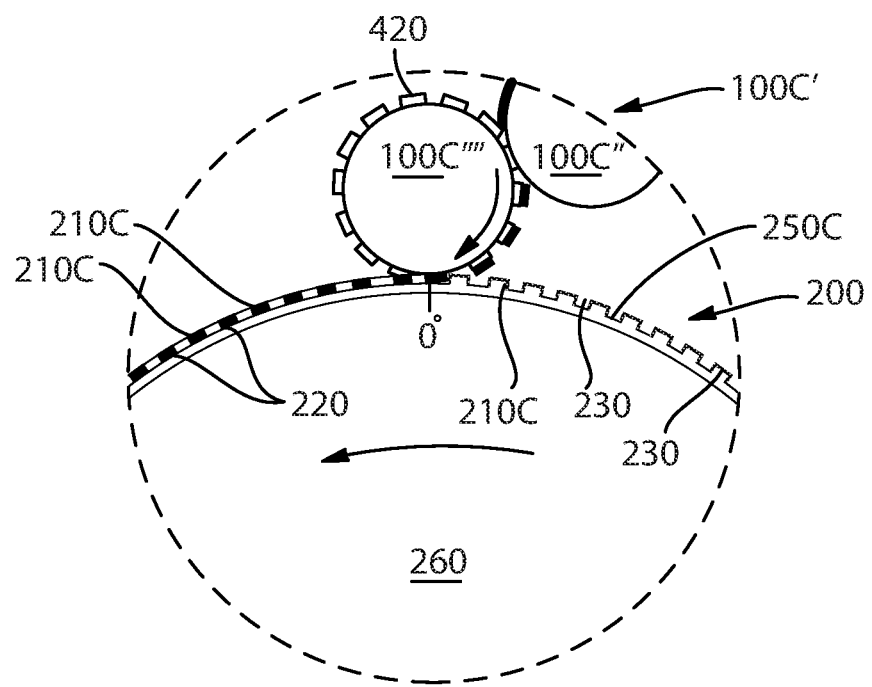
FIG. 5B is an expanded view of the region labeled 5B in FIG. 5A.

As shown in FIG. 5A, gravure roll 200C can be provided with a coater applicator 100C' in the form of a series of metering rolls 100C', 100C", and 100C'" (there being no limit on the number of metering rolls present for coater application 100C'). In this embodiment the final metering roll 100C'" can be provided with a surface comprising a plurality of protrusions 420 disposed upon a surface thereof. As represented in FIGS. 5A and 5B, it is believed that each of the plurality of protrusions 420 disposed upon the surface of final metering roll 100C'" can be provided to correspond to a respective cavity 210C disposed upon the surface 230C of shell 250C. In operation the metering rolls comprising coater applicator 100C can ultimately dispose fluid 110C upon each protrusion 420 disposed upon final metering roll 100C'". The fluid 110C disposed upon each protrusion 420 can then be transferred into a respective cavity 210C disposed upon the surface 230C of shell 250C cooperatively associated thereto.

In operation, the gravure roll 200C (namely shell 250C) rotates about axis 240 and stationary cylindrical core 260 and is coated with fluid 110C by the last of a series of metering rolls (in the exemplary embodiment provided here—final metering roll 100C'") by coater applicator 100C'. The coater applicator 100C' applies a fluid 110C, such as an adhesive, directly into a respective cavity 210C from a respective protrusion 420 disposed upon the surface of final metering roll 100C'" cooperatively associated thereto so that the fluid 110C is disposed within each cavity 210C disposed upon the surface 230C of shell 250C.

As with the embodiments described supra, the direction of rotation of the shell 250C of gravure roll 200C is indicated and the positions of the coater applicator 100C' and roll 400 (coater blade 300 not being necessarily required) are indicated in degrees of the circle which the cross-section of the gravure roll 200C. The coater applicator 100C' shown in FIGS. 5A and 5B is positioned at the top of the gravure roll 200C and, for reference purposes only, thus at 0 20 . It would be realized by one of skill in the art that coater applicator 100C' can be disposed at any position provided it is before the position of roll 400, in direction of rotation.

A source of positive pressure is supplied to the manifold formed by the central bore 290, channel 270, and gap 280 as the shell 250C rotates about axis 240 of gravure roll 200C. In turn, each cavity 210C is brought successively in register with the channel 270 and gap 280 so that as the shell 250C rotates about axis 240 and stationary cylindrical core 260, positive pressure is injected through the channel 270 from central bore 290 through gap 280 and into each cavity 210C thereby displacing any extruded fluid 220 disposed therein (either in the form of a droplet or aggregation 310) onto web material or article 500 in a pattern determined by the arrangement of the cavities 210C.

Figure 6:
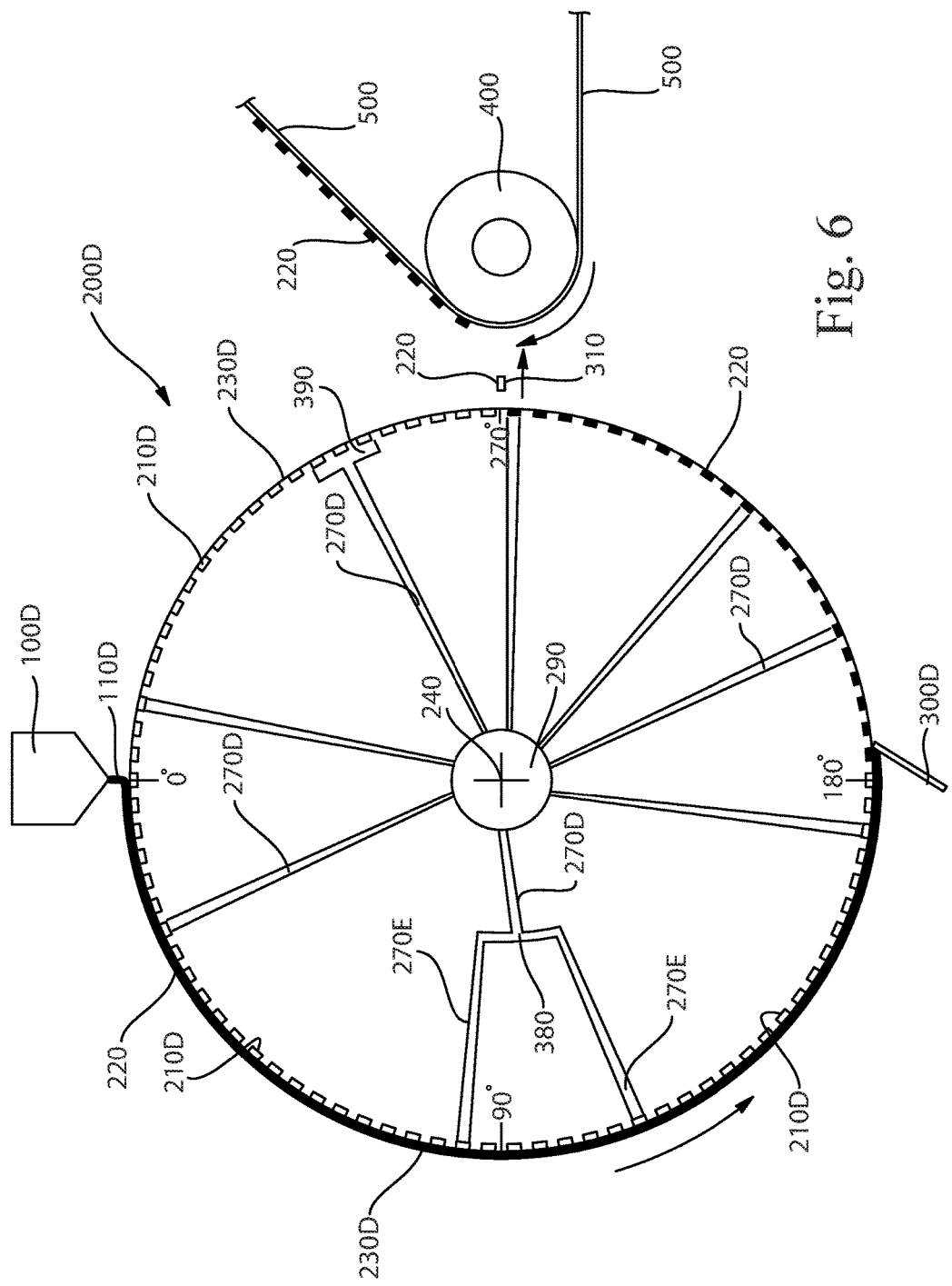
FIG. 6 is a cross-sectional view of still another exemplary equipment and process for the non-contact printing of actives onto web materials and articles according to the present disclosure.

As shown in FIG. 6, gravure roll 200D can be provided with any type of coater applicator 100D. It is believed that one of skill in the art could provide coater applicator 100D in the form of a slot extruder, spray coater, or even as a series of metering rolls. In operation, the gravure roll 200D rotates about axis 240 and is coated with fluid 110D by coater applicator 100D. The coater applicator 100D can apply a fluid 110D, such as an adhesive, onto the surface 230D of gravure roll 200D so that the fluid 110D is disposed upon the surface 230D and at least disposed within each cavity 210D disposed upon the surface 230D of gravure roll 200D. A coater blade 300D is also shown in FIG. 6, which helps push fluid into the cavities 210D.

As shown, gravure roll 200D is provided with a central longitudinal axis 240, about which the gravure roll 200D may rotate. The gravure roll 200D may further comprise a network of channels 270D for transmitting a positive pressure from the interior region (for example central bore 290) of the gravure roll 200D to the cavities 210D disposed upon surface 230D. Each channel 270D may sub-divide into a plurality of sub-channels 270E. In one embodiment, a channel 270D may be associated with one or more sub-channels 270E which extend from the channel 270D at a junction 380. Each channel 270E may be associated with one or more sub-channels 270E. In one embodiment, a channel 270D may divide into a series of sub-channels 270E. The channels 270D and sub-channels 270E may each be enclosed substantially cylindrical elements having generally uniform cross-sections along their respective lengths.

The channels 270D may be associated by any suitable means, such as gluing, welding or similar attachment operation or may be integrally formed with one another, or combinations thereof. Further, each point of association between channels 270D may comprise a junction 380. The junction 380 may be formed to provide a smooth transition from one channel 270D to another in order to prevent turbulence. A smooth transition may be achieved for example by rounding the edges of the junction 380 or associating the channels 270D such that they are not aligned end-to-end creating a sharp edge (e.g., a 90 degree angle). In other words, the channels 270D may be associated away from one or both of their ends. One of skill in the art will recognize how to design the junction 380 to achieve the desired flow.

Still referring to FIG. 6, the channels may begin at an inlet disposed in communicative, fluid engagement with central bore 290 and terminate at a point of entry into cavity 210D disposed within gravure roll 200D. Positive pressure may flow through the channels 270D and/or any associated sub-channels 270E, entering at a point in fluid communication with central bore 290, traveling from the central bore 290 through the channels 270D and sub-channels 270E (if any) to a fluid exit point in a respective cavity 210D. The central bore 290 may be in fluid communication with one or more channel 270D, and each channel 270D may be in fluid communication at least one cavity 210D. In one non-limiting example, each channel 270D is in fluid communication with one cavity 210D. In another non-limiting example, each channel 270D is in fluid communication with at least two cavities 210D. In another non-limiting example, one channel 270D is in fluid communication with one or more sub-channels 270E, and each sub-channel 270 is in fluid communication with one or more cavities 210D. A network of channels 270D and/or sub-channels 270E can resemble one or more trees that begins with a channel 270D and may extend—directly or through one or more sub-channels 270E—in a substantially radial manner to the surface 230D of gravure roll 200D through at least on cavity 210D.

A given network of channels 270D may continue to divide, such that a given individual 'tree' has n levels of branching, where n is an integer and the starting level, level 0, occurs when an initial channel 270D associates with the central bore 290. In a non-limiting example, a network of channels 270D can divide in accordance to constructal theory and/or vascular scaling laws, such as those disclosed in Kassab, Ghassan S., "Scaling Laws of Vascular Trees: of Form and Function", *Am. J. Physiol. Heart Cir. Physiol,* 290:H894-H903, 2006.

Figure 7:
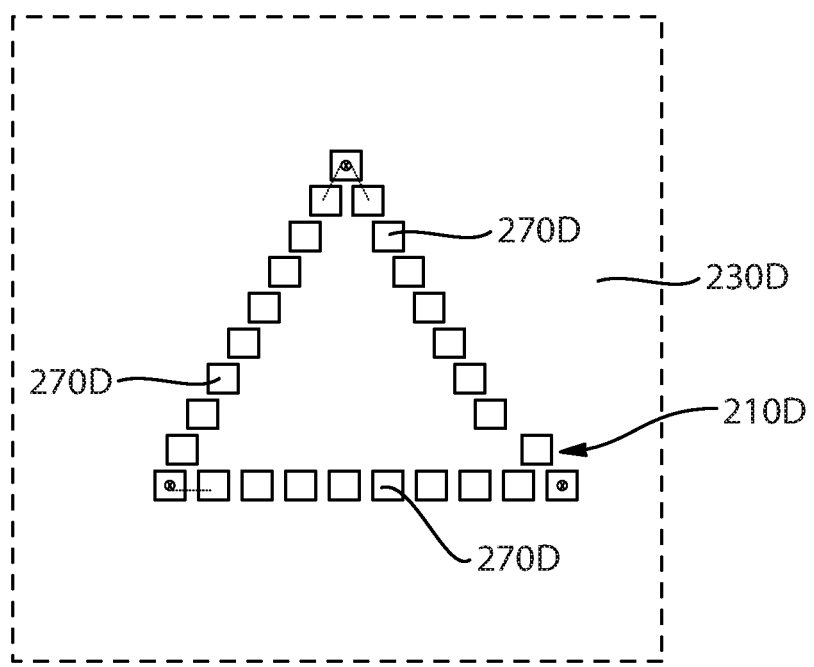
FIG. 7 is a plan view of an exemplary portion of the surface of an exemplary gravure roll suitable for use with the equipment and process for the non-contact printing of actives onto web materials and articles according to the present disclosure.
Figure 8:
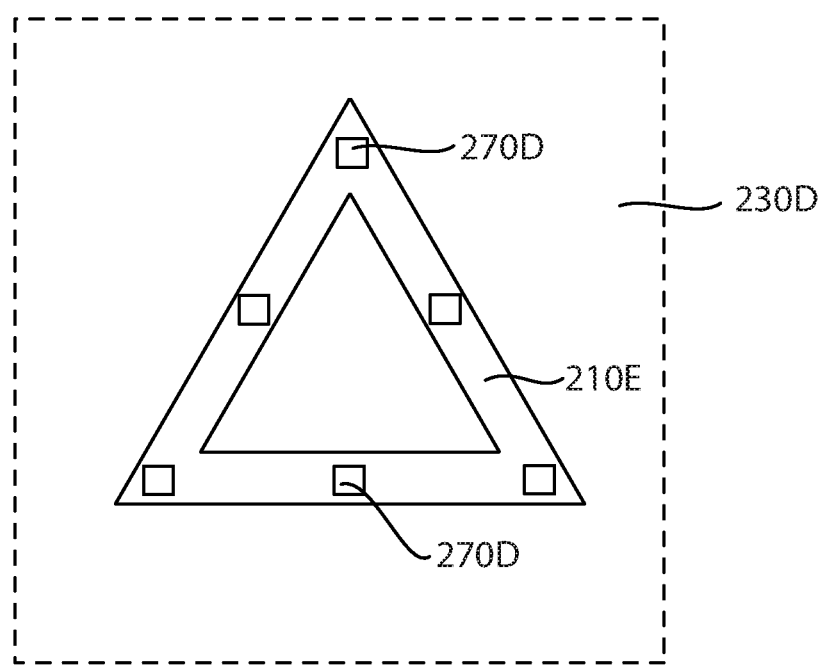
FIG. 8 is a plan view of another exemplary portion of the surface of an exemplary gravure roll suitable for use with the equipment and process for the non-contact printing of actives onto web materials and articles according to the present disclosure.

The exit of any particular channel 270D into a respective cavity 210D (shown in FIGS. 7 and 9), a plurality of channels 270D into a respective cavity 210E (shown in FIGS. 8 and 10), or a plurality of sub-channels 270E into a respective cavity 210D (shown in FIGS. 8 and 11) may be an opening of any size or shape suitable to permit a positive pressure to exit the channel 270D or sub-channel 270E in a controlled manner as dictated by the requirements of the process demanding the egress of fluid 110D disposed within cavity 210D, the web material or article 500 on which the fluid 110D is being deposited, and the amount and placement of the fluid 110D on the web material or article 500, all of which can be predetermined by a person of skill in the art. In one non-limiting example, the point of exit for a positive pressure disposed within a channel 270D or sub-channel 270E into a cavity 210D can have an aspect ratio of at least 10. The aspect ratio is typically the ratio between the depth of the exit point into a cavity 210A (in the z-direction) and a dimension or diameter located in the x-y plane of the exit point into the cavity 210A. By limiting the area of the positive pressure into cavity 210D, the flow of fluid and/or the fluid deposition may be controlled more precisely.

Additionally, it can be advantageous to provide an entry point into cavity 210D and an exit point of positive pressure from a respective channel 270D or sub-channel 270E that are conterminous, that is, the respective channel 270D or sub-channel 270E simply ends at an opening into the interior portion of a respective cavity 210D.

As shown in FIG. 12, it can also be beneficial to provide for one or more of the exit points of one or more channels 270D or sub-channels 270E to further comprise a reservoir 390. Positive pressure may collect within an inner portion of the reservoir 390 in an effort to supply positive pressure to one or more cavities 210D. The reservoir 390 may be in any shape suitable for the supply of positive pressure to one or more cavities 210D. Non-limiting examples of suitable shapes include cubic, polygonal, prismatic, round or elliptical. As can be seen in an exemplary portion of the surface of an exemplary gravure roll 200D of FIG. 7, a reservoir could be suitably adapted to provide positive pressure to one, or a plurality of points within a given cavity 210D disposed upon the surface 230D of gravure roll 200D.

As depicted in FIG. 12, the reservoir 390 may have a first side and a second side substantially opposite the first side. The first side may be associated with a channel 270D, a plurality of channels 270D or a plurality of sub-channels 270E. The first side may further comprise a single entry point through which positive pressure can enter. The second side may be associated with or integral with the cavity 210D. In one embodiment, the second side can comprise a plurality of discrete openings which serve as exit points from reservoir 390 into cavity 210D. In other words, the inner portion of reservoir 390 may be at least partially hollow and the second side of reservoir 390 may be partially solid such that openings that are coterminous with cavity 210D may be formed therein.

It was surprisingly found that a suitable gravure roll 200D, such as that depicted in FIG. 6, can be manufactured in the form of a uni-body construction. Such uni-body constructions typically enable building parts one layer at a time through the use of any form of, including any known, additive manufacturing techniques including, but not limited to, SLA/stereo lithography, SLM/Selective Laser Melting, RFP/Rapid freeze prototyping, S LS/Selective Laser sintering, SLA/Stereo lithography, EFAB/Electrochemical fabrication, DMDS/Direct Metal Laser Sintering, LENS®/Laser Engineered Net Shaping, DPS/Direct Photo Shaping, DLP/ Digital light processing, EBM/Electron beam machining, FDM/Fused deposition manufacturing, MJM/Multiphase jet modeling, LOM/Laminated Object manufacturing, DMD/ Direct metal deposition, SGC/Solid ground curing, JFP/ Jetted photo polymer, EBF/Electron Beam Fabrication, LMJP/liquid metal jet printing, MSDM/Mold shape deposition manufacturing, SALD/Selective area laser deposition, SDM/Shape deposition manufacturing, combinations thereof, and the like. However, as would be recognized by one familiar in the art, such a uni-body gravure roll 200D can be constructed using any form of additive manufacturing technologies by combining them with other techniques known to those of skill in the art such as casting. As a non-limiting example, the "inverse roll" or the desired channels 270D and/or sub-channels 270E desired for a particular gravure roll 200D format could be fabricated, and then the desired gravure roll 200D material could be cast around the desired channel fabrication. If the channel fabrication was made of hollow channels, the gravure roll 200D would be created. A non-limiting variation of this would be to make the channel fabrication out of a soluble material which could then be dissolved once the casting has hardened to create the gravure roll 200D.

In still yet another non-limiting example, sections of the gravure roll 200D could be fabricated separately and combined into a final gravure roll 200D assembly. This can facilitate assembly and repair work to the parts of the gravure roll 200D such as coating, machining, heating and the like, etc. before they are assembled together to make a complete contact printing system such as gravure roll 200D. In such techniques, two or more of the components of a gravure roll 200D commensurate in scope with the instant disclosure can be combined into a single integrated part.

By way of non-limiting example, the gravure roll 200D having a plurality of channels 270D, sub-channels 270E, and/or plurality of reservoirs 390 can be fabricated as an integral component. Such construction can provide an efficient form for forming the required circuits forming channels 270D and/or sub-channels 270E without the complexity of multi-part joining and sealing. The resultant gravure roll 200D, shown in FIG. 6, can provide for the fluid communication of a positive pressure into a desired cavity 210D to be manufactured in situ to include structure that is integrated. As shown in FIG. 12, each channel 270D and/or sub-channels 270E can be provided with multiple outlets to individual shaped reservoirs 390 underlying a respective cavity 210D and/or the gravure roll 200D surface 230D.

Alternatively, and by way of another non-limiting example, the gravure roll 200D could similarly be constructed as a uni-body structure where fluid communication is manufactured in situ to include an integrated structure that can include channels 270D, sub-channels 270E, and/or reservoir 390. One or more channels 270D and/or sub-channels 270E can then be provided to fluidly communicate a positive pressure from a central bore 290 to the cavity 210D without the need of a individual shaped reservoirs 390, but instead each cavity 210D disposed upon the surface 230D of gravure roll 200D could be directly fed from any single channel 270D or sub-channel 270E whose distal end opens into the desired cavity 210D disposed upon the surface 230D of gravure roll 200D having a desired size and location upon the surface 230D of gravure roll 200D.

Figure 13:
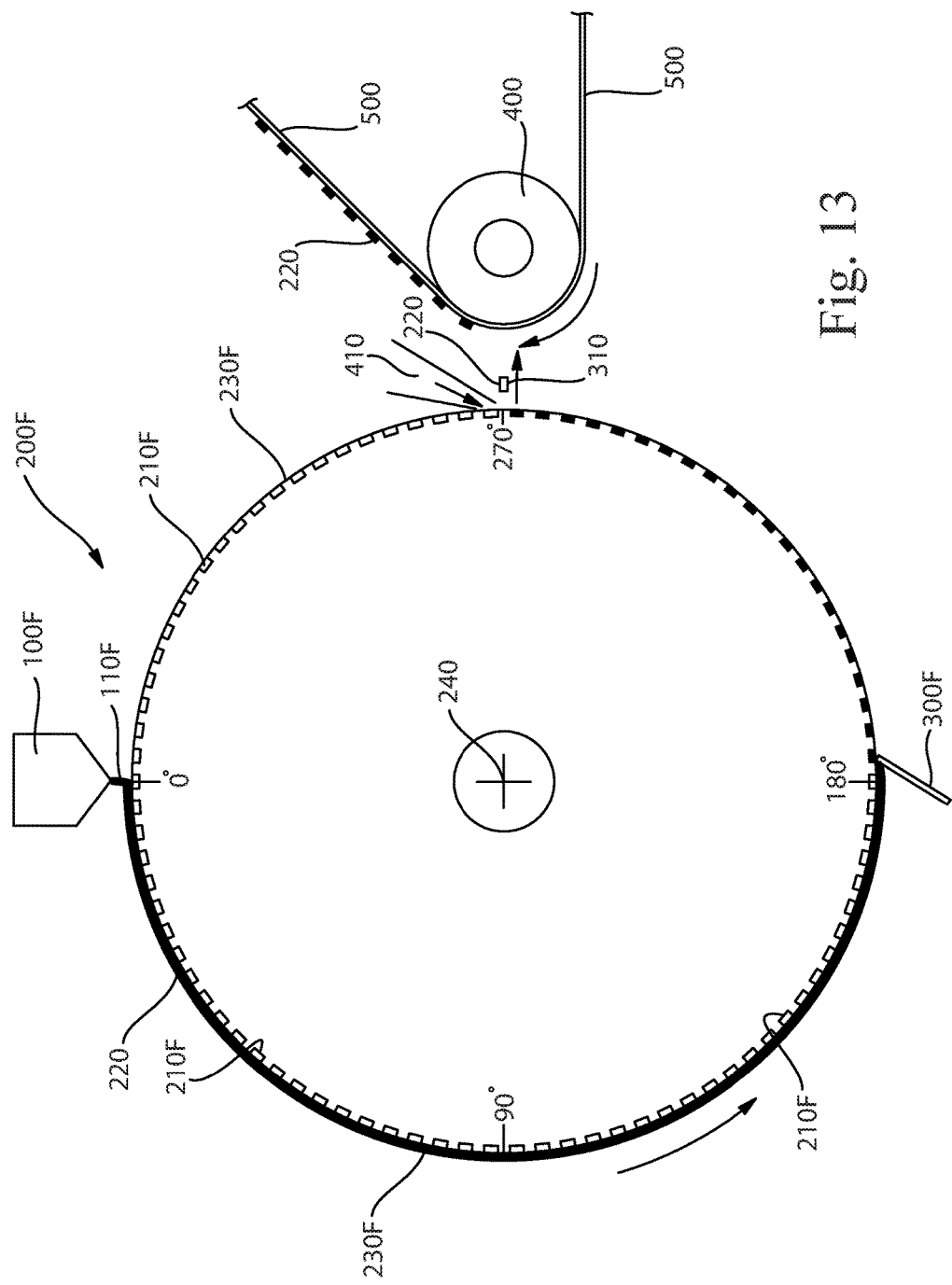
FIG. 13 is a cross-sectional view of still another exemplary equipment and process for the non-contact printing of actives onto web materials and articles according to the present disclosure.

As shown in FIG. 13, gravure roll 200F can be provided with any type of coater applicator 100F. It is believed that one of skill in the art could provide coater applicator 100F in the form of a slot extruder, spray coater, or even as a series of metering rolls. In operation, the gravure roll 200F rotates about axis 240 and is coated with fluid 110F by coater applicator 100F. The coater applicator 100F can apply a fluid 110F, such as an adhesive, onto the surface 230F of gravure roll 200F so that the fluid 110F is disposed upon the surface 230F and at least disposed within each cavity 210F disposed upon the surface 230F of gravure roll 200F.

As shown in FIG. 13, the surface 230F gravure roll 200F can be contacted by coater blade 300F. Coater blade 300F can contact the surface 230F gravure roll 200F so that the pressure exerted by the coater blade 300F upon the surface 230F of gravure roll 200F can be kept constant and spread out the extruded fluid 220 and also push the extruded fluid 220 into the cavities 210F disposed within the surface 230F of gravure roll 200F.

As the gravure roll 200F rotates about axis 240 200, each cavity 210F having fluid 110F disposed therein are each brought successively in register with an air knife 410, which is arranged so that the outer end of the cavities 210F are adjacent that region of the roll 400 which is in contact with the web material or article 500 disposed thereabout. As a result, as the gravure roll 200F rotates about axis 240, a positive pressure ejected by air knife 410 contacts the surface 230F of gravure roll 200F and causes the separation of any fluid 110F disposed within cavity 210F and directs the resulting droplet or aggregation 310 of fluid 110F toward roll 400 and onto web material or article 500 in a pattern determined by the arrangement of the cavities 210.

One of skill in the art will readily recognize and appreciate that air knives are normally used in manufacturing to separate lighter or smaller particles from other components for use in later or subsequent steps, post manufacturing parts drying and conveyor cleaning, part of component cleaning. A typical air knife provides a high intensity, uniform sheet of laminar airflow sometimes known as streamline flow.

An exemplary air knife can comprise a pressurized air plenum containing a series of holes or continuous slots through which pressurized air exits in a laminar flow pattern. The exit air velocity then creates an impact air velocity onto the surface of whatever object the air is directed. This impact air velocity can range from a gentle breeze to greater than Mach 0.6 (40,000 ft/min) to alter the surface of a product without mechanical contact. Air knives can be used to remove liquids, control the thickness of liquids, dry the liquid coatings, remove foreign particles, cool product surfaces or create a hold down force to assist in the mechanical bonding of materials to the surface. Electrical currents from anti-static bars can also be injected into the exit air knife stream to neutralize the static electricity charge on some surfaces.

As provided herein, the air knife 410 is positioned stationary relative to gravure roll 200F so that the fluid 110A in the form of extruded fluid 220 passes through the air velocity air stream. In some embodiments, one of skill in the art will understand that the gravure roll 200F can be provided stationary relative to air knife 410 that can be provided to reciprocate or rotate over the surface 230F of gravure roll 200F.

Exemplary air knives can range from 0.25 to 200 inches (6.4 to 5,080.0 mm) in length and be provided with a discharge air slot or holes ranging from 0.001 to 0.25 in (0.025 to 6.350 mm). A suitable stationary air knife configuration can provide from one to a dozen air knives depending on the application criteria. Positive pressure is directed through the air knife 410 slots via an air generator, either an industrial blower or air compressor, to deliver the predetermined exit air volume and velocity needed. A suitable air knife 410 can be a compressed air powered air knife (utilizing the Coandă effect that entrains ambient air into the high velocity stream to enhance the blow off effect) as well as blower powered air knives (a 'tear drop-shaped' air knife having a bulbous plenum that tapers down to a precise air discharge slot.

Figure 14:
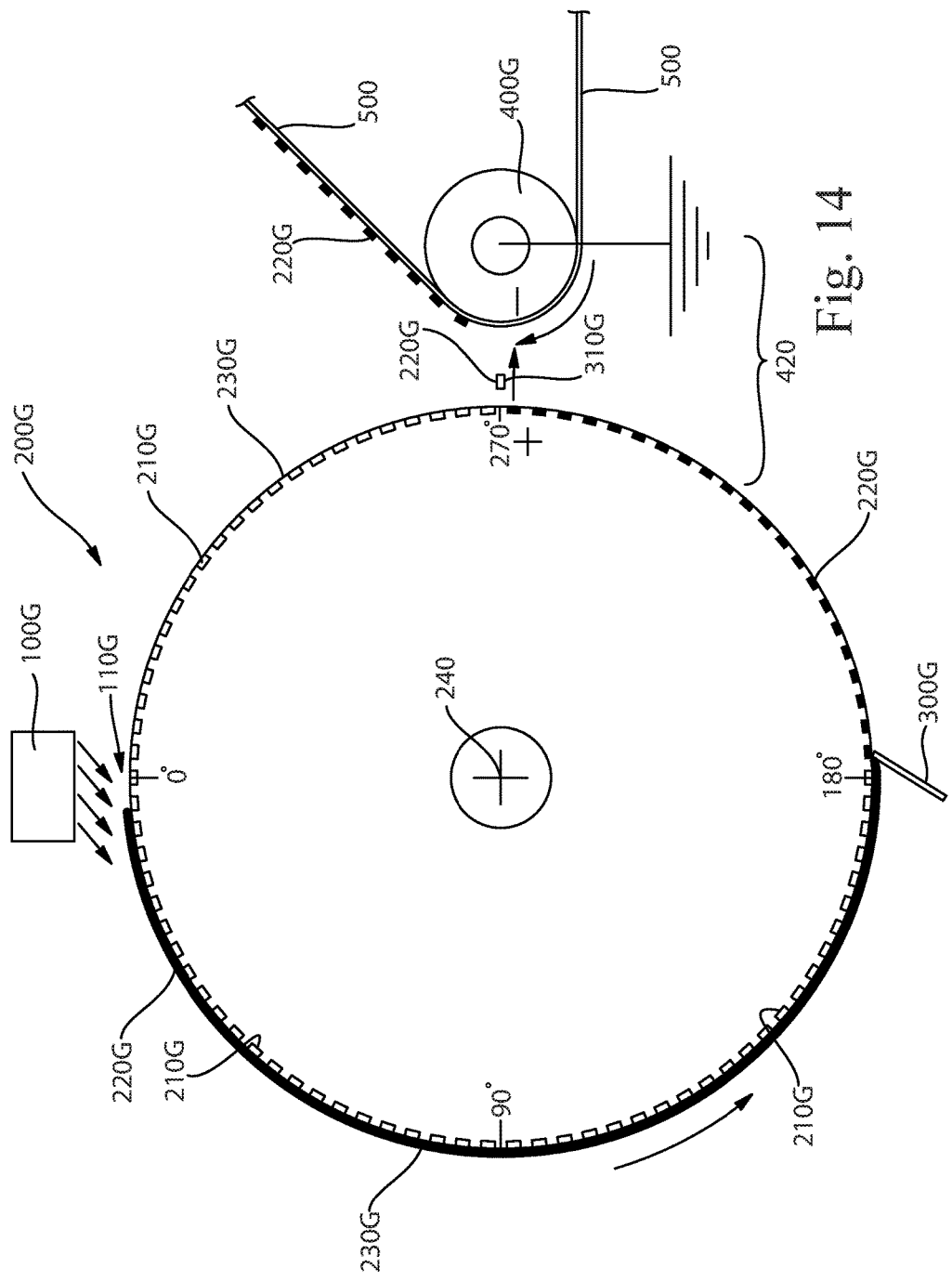
FIG. 14 is a cross-sectional view of yet still another exemplary equipment and process for the non-contact printing of actives onto web materials and articles according to the present disclosure; and, FIG. 15 is a cross-sectional view of still yet another exemplary equipment and process for the non-contact printing of actives onto web materials and articles according to the present disclosure.

In another embodiment shown in FIG. 14, gravure roll 200G can be provided with any type of coater applicator 100G. It is believed that one of skill in the art could provide coater applicator 100G in the form of a slot extruder, spray coater, or even as a series of metering rolls. In operation, the gravure roll 200G rotates about axis 240 and is coated with an electrically conductive fluid 110G by coater applicator 100G. The coater applicator 100G can apply an electrically conductive fluid 110G, such as an electrically conductive adhesive, onto the surface 230G of gravure roll 200G so that the electrically conductive fluid 110G is disposed upon the surface 230G and at least disposed within each cavity 210G disposed upon the surface 230G of gravure roll 200G.

As shown in FIG. 14, the surface 230G gravure roll 200G can be contacted by coater blade 300G. Coater blade 300G can contact the surface 230G gravure roll 200G so that the pressure exerted by the coater blade 300G upon the surface 230G of gravure roll 200G can be kept constant and spread out the extruded electrically conductive fluid 220G and also push the extruded electrically conductive fluid 220G into the cavities 210G disposed within the surface 230G of gravure roll 200G.

As the gravure roll 200G rotates about axis 240, each cavity 210G having electrically conductive fluid 110G disposed therein are each brought successively in register with a source of an electromotive force (EMF) 420. The source of EMF 420 can be arranged so that the outer end of the cavities 210G having the electrically conductive fluid 110G disposed therein are adjacent that region of the roll 400 which is in contact with the web material or article 500 disposed thereabout. As a result, as the gravure roll 200G rotates about axis 240, an EMF provided by the source of EMF 420 and providing an EMF between gravure roll 200G and roll 400G motivates the separation of any electrically conductive fluid 110G disposed within cavity 210G and directs the resulting droplet or aggregation 310G of fluid 110G toward roll 400G and onto web material or article 500 in a pattern determined by the arrangement of the cavities 210G.

Suitable electrically conductive fluids 110G can include conductive and adhesive hydrogels which are suitable to pass an electrical current. Suitable electrically conductive fluids 110G can include hydrogels having resistivities (or volume resistivities) of less than about 20,000 Ωcm at 10 Hz, or less than about 10,000 Ωcm at 10 Hz, or less than about 2,500 Ωcm at 10 Hz, where resistivity (or volume resistivity) is defined as equal to:

$$\text{Resistance } (\Omega) \times \text{Area } (\text{cm}^2) \text{ Thickness (cm)}$$

It is believed that the application of an electrically conductive fluid 110G can provide improved pattern definition of electrically conductive fluid 110G upon web material or article 500. What is meant by an improved pattern definition is that a particular fluid 220 of electrically conductive fluid 220G removed from the surface 230G (e.g., a droplet or aggregation 310G) is being contacted upon a pre-designated on a desired portion of web material or article 500.

Suitable electrically conductive fluids 110G can be made from cationic acrylates including, but are not limited to, acrylic esters of quaternary chlorides and/or sulfates, and/or acrylic amides of quaternary chlorides. Further, such suitable electrically conductive fluids 110G can be bactericidal, fungicidal, and resistant to breakdown problems due to exposure to radiation for sterilization purposes. Additionally, suitable electrically conductive fluids 110G may be arranged and stored in face-to-face contact, substantially without barriers, yet remain readily separable. Suitable electrically conductive fluids 110G include between about 15-60% by weight polymer and include sufficient buffer to maintain the pH of the hydrogel in a range of about 4.0-5.5. Other additives may also be included.

Exemplary cationic acrylates can include acryloyloxyethyltrimethyl ammonium chloride, acryloyloxyethyltrimethyl ammonium methyl sulfate, and acrylamidopropyltrimethyl ammonium chloride and can include a buffer system to help control the pH, help prevent discoloration, and/or help prevent breakdown due to the extended presence of water (i.e. help prevent hydrolysis). Additionally, conductivity enhancers (such as salts such as potassium chloride, sodium chloride, and weak organic acids) may be used.

Figure 15:
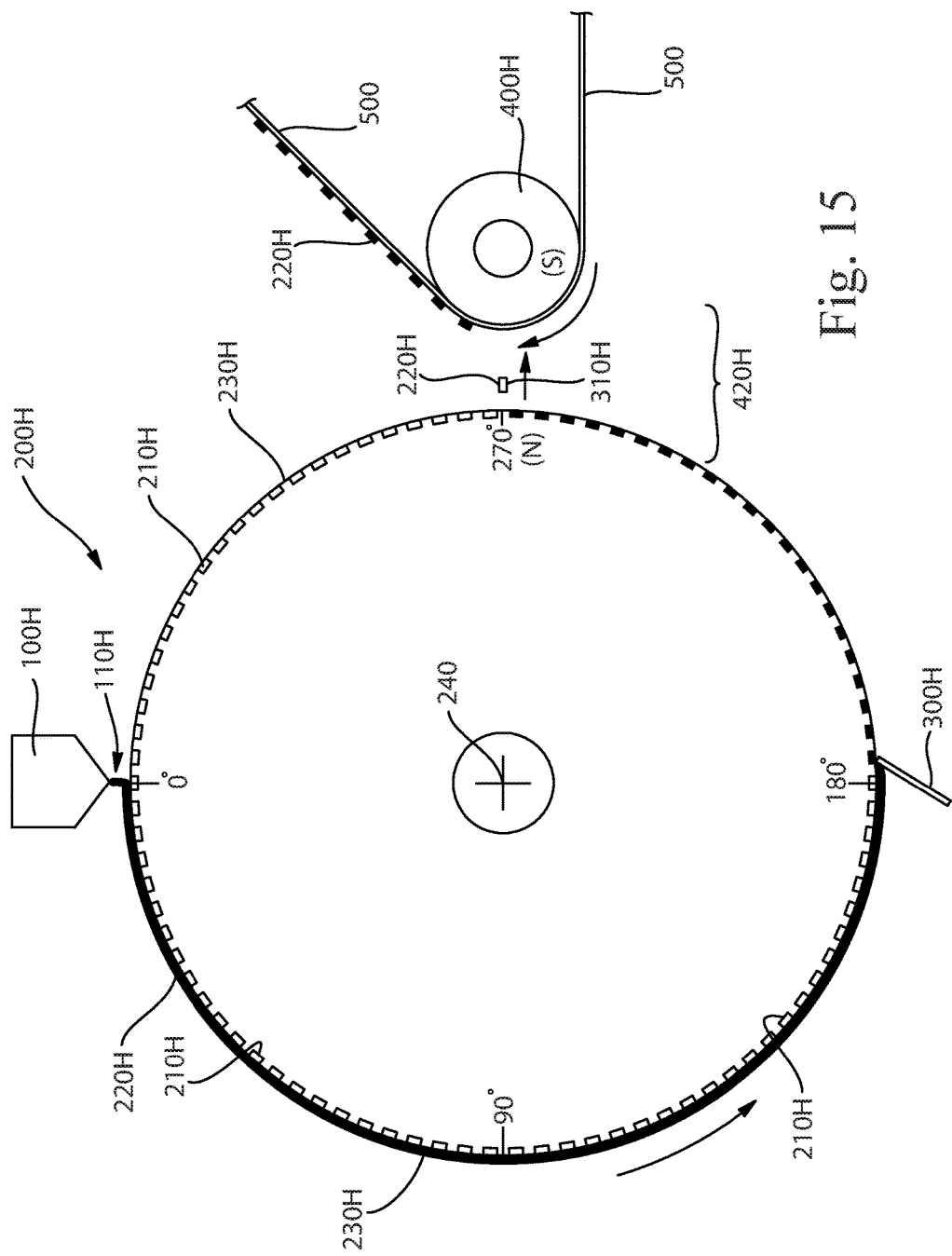

In another embodiment shown in FIG. 15, gravure roll 200H can be provided with any type of coater applicator 100H. It is believed that one of skill in the art could provide coater applicator 100H in the form of a slot extruder, spray coater, or even as a series of metering rolls. In operation, the gravure roll 200H rotates about axis 240 and is coated with a magnetically influenceable or magnetic fluid 110H by coater applicator 100H. The coater applicator 100H can apply a magnetically influenceable or magnetic fluid 110H, such as an magnetic adhesive, onto the surface 230H of gravure roll 200H so that the electrically conductive fluid 110H is disposed upon the surface 230H and at least disposed within each cavity 210H disposed upon the surface 230H of gravure roll 200H.

As shown in FIG. 15, the surface 230H gravure roll 200H can be contacted by coater blade 300H. Coater blade 300H can contact the surface 230H gravure roll 200H so that the pressure exerted by the coater blade 300H upon the surface 230H of gravure roll 200H can be kept constant and spread out the extruded magnetically influenceable or magnetic fluid 220H and also push the extruded magnetically influenceable or magnetic fluid 220H into the cavities 210H disposed within the surface 230H of gravure roll 200H.

As the gravure roll 200H rotates about axis 240, each cavity 210H having the extruded magnetically influenceable or magnetic fluid 220H disposed therein are each brought successively in register with a source of a magnetic force 420H. The source of magnetic force 420H can be arranged so that the outer end of the cavities 210H having the magnetically influenceable or magnetic fluid 220H disposed therein are adjacent that region of the roll 400H which is in contact with the web material or article 500 disposed thereabout. As a result, as the gravure roll 200H rotates about axis 240, the magnetic field disposed between roll 400H and gravure roll 200H motivates the separation of any magnetically influenceable or magnetic fluid 220H disposed within cavity 210H and directs the resulting droplet or aggregation 310H of fluid 110H toward roll 400H and onto web material or article 500 in a pattern determined by the arrangement of the cavities 210H.

Suitable magnetically influenceable or magnetic fluid 220H can include adhesives that are manufactured by adding magnetic nanoparticles into a curable glue or resin. The magnetic nanoparticles can include magnetic metal nanoparticles or magnetic metal oxide nanoparticles. The magnetic metal can include iron, cobalt, nickel, iron alloys, cobalt alloys, nickel alloys, and combinations thereof. The size of the magnetic nanoparticles can range from about 1 nanometer (nm) to about 100 nm. In some embodiments, a suitable curable glue or resin can be a light-curable glue or resin. In another embodiment, the curable glue can also be a hot-curable glue or resin.

In all embodiments, after the fluid 220 is transferred onto the web material or article 500 disposed on or about the roll 400, the gravure roll 200 rotates further to a position proximate to the coater 100 position so that the process can start again. It should be understood that this process is typically done in a continuous manner.

In the embodiments shown in FIGS. 1-13, the fluid 110 can include polyfluorinated polymers. Preferred are coatings comprising a compound similar to Teflon, available from DuPont or similar to NF(3), available from Nanosol GmbH. Preferred are coating comprising Teflon, available from DuPont, and/or NF(3), available from Nanosol GmbH.

As shown in FIGS. 1-15, the web material or articles 500 are supported roll 400 that can be provided as a rotatable roll with an endless surface. Roll 400 preferably rotates so the web material or article 500 are rotated and positioned proximate to gravure roll 200 with the roll 400. One of skill in the art could provide roll 400 as a rotating belt or a roll, such as a cylindrical roll.

The roll 400 has preferably a surface with a Shore A hardness value ranging from 25 to 90, or from 25 to 60, or even to 50. Roll 400 can be provided with a surface made of a resilient material, such as rubber. This is the Shore A hardness value as measured by the method ASTM D-2240, version 2000.

In one embodiment, roll 400 can be cooled. Appropriate cooling can be accomplished with the use of a cooling element having a temperature control. Roll 400 can be provided with a surface temperature of at least 20° C., or at least 50° C., at least 80° C., or at least 100° C. less than the surface temperature of gravure roll 200. Roll 400, or at least the surface thereof, is cooled to a temperature ranging from between 0° C. and 30° C., or from 0° C. to 15° C.

Because the process described supra is such that fluids 110 comprising sticky materials can be transferred with reduced stringing and with improved accuracy and efficiency, the aforementioned process can be done very fast. This has as advantage that even when the web material or articles 500 onto which fluid 110 is applied have a melting point below the temperature of the web material or articles 500 (or any incorporated transfer tool), the fluid 110 can still be heated to such high temperatures, without causing the web material or articles 500 to melt or deform. Thus, a process herein can provide a process temperature, or the temperature of the fluid 110 that is higher than the melting temperature of the web material or articles 500. The temperature difference can for example be at least 10° C., or at least 20° C., or least 30° C., and it can be as much as 80° C., or up to 60° C., or up to 45° C.

Roll 400 can have any dimension, and can be dependent on the dimension of the gravure roll 200 and the dimension of the web material or articles 500 supported and rotated by the roll 400. Further, roll 400 is positioned past the coater blade 300, in the direction of rotation of the gravure roll 200. Additionally, roll 400 may be under vacuum so that the vacuum is applied through the roll 400 to the web material or articles 500. This can assist the affixation of the web material or articles 500 on the roll 400 during rotation and when proximate to gravure roll 200.

The web material or articles 500 obtainable by the apparatus and process of the present disclosure, can have the fluid 110 applied in a homogeneous even layer, or in a pattern where the covered areas of the pattern (e.g. dots) have about the same amount of active material per surface area. Alternatively, the present apparatus and process can facilitate the application of the fluid 110 in a pattern that can selectively deposit the fluid 110 onto the web material or articles 500 where the fluid 110 is preferentially required by the desired end use of the web material or articles 500. Such a selected pattern of deposition can be facilitated by the placement of the cavities 210 upon the surface 230 of the gravure roll 200 as well as adjusting the depth of a particular cavity 210 or plurality of cavities 210 relative to the surface 230 of gravure roll 200. Other manners that could conceivably provide a selected pattern of deposition of a fluid 110 onto a web material or articles 500 can also include varying the rotational velocity of gravure roll 200 and/or roll 400. Such a selected pattern of deposition can provide a differential basis weight of fluid 110 upon the web material or article 500. The selected pattern can be homogenous (fluid 110 applied equally upon web material or article 500) or non-homogeneously (fluid 110 applied unequally upon web material or article 500) to allow for the placement of adhesive so that they have different basis weights relative to any portion of the surface of the web material or articles 500.

A selected pattern of deposition can be reflected by the Coefficient of Variation (CoV) of the height of the applied fluid 110 and/or the CoV of the area of the applied fluid 110. The CoV is defined as standard deviation divided by the average value, or the so-called reduced standard deviation, of the amount of fluid 110 of a certain area on which the active material is applied. For example, when the web material or articles 500 comprises a pattern of homogeneous dots, the homogeneous character is defined by the height-of-dot-CoV and area-of-dot-COV, for a certain area having a certain number of dots (thus, the CoV is being calculated for the dot area and the dot height measurements). In the present disclosure the dot height CoV (%) for a surface area of the web material or articles 500 having 30 dots can be less than 10%, or less than 6%, or less than 5.5% or less than 5%, or less than 4.4%. The CoV (5) for the area per dot can be less than 10%, or less than 8%, or less than 7%, or less than 6%. The CoV can be determined from the area and the height of single dots, measured with Mikro CAD topographer from GFM. Area and height of single dots could be determined using standard equipment such as BioRad MRC 600 laser scanning confocal microscopy.

The contact angle can be determined by use of the sessile-drop method. A drop of the fluid 110 in liquid state (e.g. melted) is applied onto a sample of the tool with an electronically software-controlled syringe used to generate the drop (the sessile drop). The tool-sample and the syringe are fixed in an electrically controlled temperature control chamber (TC 350 ex Dataphysics). The resulting sessile drop is exposed to diffused light from one side and observed from the other side by means of a CCD camera of a video-supported contact goniometer (OCA20 ex Dataphysics). The contact angle is consequently measured according to the following steps:

1. Record a digital image of the sessile drop with the CCD camera.
2. Determine the position of the base line and the drop contour by calculating the difference of the brightness of one image spot to the adjacent area. The drop contour and the base line result from the position of the maximum differences between brightnesses (i.e. of the maximum contrast).
3. Match the drop contour line to the measured drop outline with the Young-Laplace method. (In the Young-Laplace method, a curve is matched that exactly follows the drop outline. The drop shape is determined by the force equilibrium between surface tension and gravity. In the Young-Laplace method, the corresponding equation is solved numerically, with the solution being adapted to the previously determined drop outline by means of a parameter.)
4. Measure the contact angle as the angle between the surface of the tool-sample and the tangent to drop shape in the contact point with the surface.

The measurement can be done with a video-supported contact goniometer OCA20 from Dataphysics which determines the (static) contact angle according to the sessile drop method.

The peel force separating adhesively conjoined portions of a room temperature assembled article can be determined by placing the assembled article on a rigid support with the surface with the active material facing upward, away from the support. The sample is fixed to the support by grips in a tightly and wrinkle-free manner. A piece of cotton (100%), known as Weave Style no.429W, available from Loeffler, is placed on top of the surface with the adhesive material so that one end of the cotton sample extends about 25 mm from the end of the sample with adhesive material. A weight is placed on the formed sample-cotton combination for 30 seconds so that the whole combination is covered. A weight of 26-27 g/cm² is applied.

A Zwick tensile tester (available from Zwick GmbH) is used to measure the peel force required to remove the cotton from the sample. The support and sample covered by cotton is placed in the lower clamp of the tensile tester and the tail end of the cotton (the one opposite to the free 25 mm specified above) is placed in the upper clamp of the tensile tester. The Zwick tensile tester is set on a speed of 40 inch/minute. Typically the clamps are 250 mm spaced apart.

Within 1 minute after removal of the compression weight, the tensile tester is started and measures the force required (to peel off the cotton) along the displacement of the upper clamp, which moved in an angle of 18020 with the sample. The peel force is calculated as the average of the force peaks over a 5 inch path. The first 1.0 inches and last 1.5 inches of the measurement are not taken into account by the calculation of the peel force, to avoid periods of acceleration and deceleration.

Viscosity can be measured using the method ASTM D3236-88.

Elastic modulus G' and the viscous modulus G", is measured by the method ASTM D4440-95, using flat plates oscillating at 1 Hz.

Surface energy can be measured by determining the contact angle of a liquid to a layer of the active material, in solid state according to the sessile drop method. The surface energy can be calculated from the measured contact angles using the Owens-Wendt-Rabel-Kaelbe method. The contact angle on a layer of active material for each liquid is calculated using the method described herein where the layer is fixed in a liquid temperature control chamber (TFC100) in the absence of air and under dry nitrogen. Such an even layer of active material is obtained by prepared by applying a layer of the active material in molten state onto a glass slide, ensuring there are no air bubbles entrapped in the melt.

A web material or articles 500 can comprise an absorbent article. An absorbent article can comprise the specific materials and adhesives as described above. The absorbent article can be a disposable absorbent article, or component thereof. The components can include one or more of: a wearer facing surface comprising a liquid permeable substrate of fibrous or film-like structure (i.e., top-sheet); a garment facing surface comprising a liquid impermeable substrate (i.e., a back-sheet) that can be moisture vapor permeable and hence breathable; and, an absorbent structure placed between the wearer facing surface and the garment facing surface (i.e., an absorbent core (all referred to herein as components). Absorbent articles for absorbing liquid can include sanitary napkins, panty liners, adult or baby diapers, and/or incontinence products.

Absorbent articles can comprise any of the components or features usual in the art (e.g., side-wrapping elements, side flap components, or wings, as well as any sort of extensibility or elastication features). The production of absorbent articles provides for several adhesive connections to be formed. For example, a typical sanitary napkin or panty liner can comprise an adhesive area on the garment facing surface of the back-sheet providing panty-fastening. The adhesive can be covered by a release paper, wrapper or the like prior to use of the article and removed prior to attachment to a garment.

Each component of an absorbent article can comprise at least one layer that has a wearer facing surface and a garment-facing surface. Garment-facing surfaces form a common interface with the wearer-facing surface of an adjacent component or layer. The components or layers are joined together across this common interface. In this manner, the top-sheet is joined to the absorbent core, and the core is joined to the back-sheet. Furthermore, the top-sheet, back-sheet, and/or any core components can comprise more than one layer and these layers may also be similarly joined. Additionally, the top-sheet may be directly or indirectly joined to the back-sheet at the periphery of the absorbent article and in the wings, if present. Furthermore, the garment facing surface of the back-sheet can provide the surface to which the absorbent article is joined to the garment of the user of the product to provide the panty fastening adhesive. If the product is a winged product, the wings are also provided with adhesive to secure the wings to the garment-facing surface of the undergarment. These surfaces are typically provided with protective covers that are removed prior to use.

Thus, an absorbent article can provide at least one of the wearer or garment facing surfaces of the top-sheet, core, or back-sheet components to comprise a fluid as described herein. In one embodiment, at least the garment-facing surface of the back-sheet is applied with an adhesive area according to the present disclosure. At least the garment facing surface of the back-sheet and at least one other surface are joined to another by application of an adhesive area and preferably all of the common interfaces of the components of the article are joined together by the application of adhesive.

The absorbent articles of the disclosure will now be described with reference to the application of a panty-fastening adhesive to the garment-facing surface of the back-sheet. However, as discussed herein above the disclosure is equally applicable for the adhesion of the common interface between any of the other surfaces of the components of the absorbent article. Typically, at least a portion of the garment-facing surface of the back-sheet is coated with typically a pressure sensitive adhesive as described herein above, to form the panty fastening adhesive. Prior to use of the absorbent article the panty fastening adhesive is typically protected from contamination and from adhering to another surface where this is not desired, by a protective cover means such as a silicone coated release paper, a plastic film or any other easily removable cover. The protective cover means can be provided as a single piece or in a multitude of pieces e.g. to cover the individual adhesive areas. It also can perform other functions such as provide individualized packaging for the article or provide a disposal function. Any commercially available release paper or film may be used. Suitable examples include BL 30MG-A SILOX EI/O, BL 30 MG-A SILOX 4 P/O available from Akrosil Corporation, and M&W films available from Gronau in Germany, under the code X-5432.

If protective side flaps or wings-are present then they may also be provided with optional fasteners thereon for additional security. The fasteners assist the protective side flaps to remain in position after they have been wrapped around the edges of the crotch surface of the undergarment by adhering to the garment-facing surface of the undergarment. Hence, the adhesive area applied in the wings is typically independent from the adhesive area applied as the so-called panty fastening adhesive on the back-sheet. The fasteners of the side flaps may also be applied with adhesive areas according to the present disclosure and/or using the process of the disclosure, and are typically also covered with a protective cover means.

The top-sheet is preferably compliant, soft feeling, and non-irritating to the wearer's skin. The top-sheet also can have elastic characteristics allowing it to be stretched in one or two directions in portions of the top-sheet or throughout its extension. Further, the top-sheet is typically fluid pervious permitting fluids (e.g., menses and/or urine) to readily penetrate through its thickness. A suitable top-sheet can be manufactured from a wide range of materials such as woven and non-woven materials; polymeric materials such as apertured formed thermoplastic films, apertured plastic films, and hydro-formed thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers. Preferred top-sheets for use in absorbent articles can be selected from high loft nonwoven top-sheets and apertured formed film top-sheets. An exemplary top-sheet for the present disclosure comprises the formed film described in one or more of the above patents and marketed on sanitary napkins by The Procter & Gamble Company of Cincinnati, Ohio as "DRI-WEAVE". The body surface of the formed film top-sheet can be hydrophilic so as to help liquid to transfer though the top-sheet faster than if the body surface was not hydrophilic. Surfactant can be incorporated into the polymeric materials of the formed film top-sheet. This can be a sticky material as defined herein and can thus also advantageously be applied by the process of the present disclosure.

Alternatively, the body surface of the top-sheet can be made hydrophilic by treating it with a surfactant. This can also be a viscous, sticky material as defined herein and can thus also advantageously be applied by the process of the present disclosure.

The absorbent article can have an absorbent core selected from any of the absorbent cores or core system known in the art. "Absorbent core" refers to any material or multiple material layers whose primary function is to absorb, store and distribute fluid. The absorbent core can include: (a) an optional primary fluid distribution layer preferably together with a secondary optional fluid distribution layer; (b) a fluid storage layer; (c) an optional fibrous ("dusting") layer underlying the storage layer; and (d) other optional components that can be adhered together by an adhesive. Modified cellulose fibers such as the stiffened cellulose fibers and synthetic fibers including those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bi-component fibers, tri-component fibers, mixtures thereof, and the like can be used. The fiber surfaces can be hydrophilic. The storage layer can also include filler materials, such as Perlite, diatomaceous earth, Vermiculite, etc., to improve liquid retention.

Back-sheets prevent absorbed matter and/or the matter contained in the absorbent structure from wetting articles that contact the absorbent product (e.g., underpants, pants, pajamas, and undergarments). The back-sheet can be impervious to liquids (e.g. menses and/or urine) and can be manufactured from a thin plastic film and other flexible liquid impervious materials. "Flexible" refers to materials that are compliant and readily conform to the general shape and contours of the human body. The back-sheet can have elastic characteristics allowing stretch in at least one direction. A back-sheet can extend across the absorbent structure and can extend into and form part of or all of side flaps, side wrapping elements, or wings. The back-sheet can comprise a woven or nonwoven material, polymeric films such as thermoplastic films of polyethylene or polypropylene, and/or composite materials such as a film-coated nonwoven material. Back-sheet can be a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The back-sheet is preferably embossed and/or matt finished to provide a more cloth like appearance.

All publications, patent applications, and issued patents mentioned herein are hereby incorporated in their entirety by reference. Citation of any reference is not an admission regarding any determination as to its availability as prior art to the claimed invention.

The dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for providing non-contact application of fluids onto web materials and articles, the apparatus comprising:
a gravure roll comprising:
a hollow rotating shell having a plurality of cavities disposed within the outer surface thereof;
a stationary cylindrical core having a central bore and a channel disposed therein, said central bore being disposed about an axis of said stationary cylindrical core, said channel being in fluid communication with said central bore and in fluid communication with a surface of said stationary cylindrical core, said channel having a single entry point and a single exit point and extending from said central bore to said surface of said stationary cylindrical core, said channel being capable of fluidly communicating a positive pressure from said central bore to said surface of said stationary cylindrical core;
wherein said hollow rotating shell is disposed about, and rotatable about, said stationary cylindrical core;
wherein each of said plurality of cavities disposed within said outer surface of said hollow rotating shell are rotated about said stationary cylindrical core and said axis so that a portion of each of said cavities are positioned in contacting and fluid engagement with said channel at said surface of said stationary cylindrical core and said positive pressure is fluidly communicateable from said central bore through said channel and into said cavity from said surface of said stationary cylindrical core; and,
wherein a fluid disposed within a respective cavity of said plurality of cavities disposed within said outer surface of said hollow rotating shell is removed from said respective cavity by said positive pressure when said positive pressure is fluidly communicated from said central bore through said channel and into said cavity from said surface of said stationary cylindrical core;
wherein a web or article receiving the removed fluid is positioned proximate to but spaced apart from said outer surface of said hollow rotating shell in non-contacting fashion; and
a roll, said roll being disposed proximate to said hollow rotating shell, said fluid being disposable upon a surface of said roll when said fluid disposed within said respective cavity of said plurality of cavities disposed within said outer surface of said hollow rotating shell is removed from said respective cavity by said positive pressure when said positive pressure is fluidly communicated from said central bore through said channel and into said cavity from said surface of said stationary cylindrical core.

2. The apparatus of claim 1 further comprising a coating applicator, said coating applicator disposing said fluid upon said outer surface of said hollow rotating shell.

3. The apparatus of claim 2 wherein said coating applicator further comprises a heating element.

4. The apparatus of claim 1 further comprising a coater blade, said coater blade being disposed in contacting engagement with said surface of said hollow rotating shell and capable of distributing said fluid disposed upon said surface into each of said plurality of cavities.

5. The apparatus of claim 4 wherein said coater blade is operably connected to a pivot, said pivot causing said coater blade to contact said surface of said hollow rotating shell at an angle ranging from about 4 degrees to about 45 degrees relative to said tangent of said hollow rotating shell.

6. The apparatus of claim 4 wherein said coater blade exerts a constant pressure upon said surface of said hollow rotating shell.

7. The apparatus of claim 1 wherein said stationary cylindrical core further comprises a sealing material disposed upon a surface thereof, said sealing material providing sealing engagement between said stationary cylindrical core and an internal surface of said hollow rotating shell.

8. The apparatus of claim 1 further a source of positive pressure, said source of positive pressure being operably connected and in fluid engagement with said central bore and said channel disposed within stationary cylindrical core.

9. The apparatus of claim 1 wherein said roll further comprises a web material disposed thereabout, said fluid being disposable upon said web material when said web material is disposed proximate to said respective cavity of said plurality of cavities disposed within said outer surface of said hollow rotating shell.

10. The apparatus of claim 9 wherein said web material further comprises at least one article disposed thereupon, said fluid being disposable upon said at least one article when said at least one article is disposed proximate to said respective cavity of said plurality of cavities disposed within said outer surface of said hollow rotating shell.

11. The apparatus of claim 1 wherein said roll further comprises a source of negative pressure operable connected to a surface thereof, said source of negative pressure being capable of motivating said fluid disposed from said cavity of said hollow rotating shell to said surface of said roll.

12. The apparatus of claim 1 wherein each of said cavities disposed upon said surface of said hollow cylindrical wall are successively brought in register with said channel as said hollow rotating shell orbits about said surface of said stationary cylindrical core.

* * * * *